US012680088B2

(12) United States Patent
Akahoshi et al.

(10) Patent No.: US 12,680,088 B2
(45) Date of Patent: Jul. 14, 2026

(54) MODIFIED PIGGYBAC TRANSPOSASE POLYPEPTIDE, POLYNUCLEOTIDE ENCODING THEM, INTRODUCING CARRIER, KIT, METHOD OF INCORPORATING TARGET SEQUENCE INTO CELL GENOME, AND METHOD OF PRODUCING CELL

(71) Applicant: KABUSHIKI KAISHA TOSHIBA, Tokyo (JP)

(72) Inventors: Eiichi Akahoshi, Shinagawa (JP); Emi Nozaki, Shinagawa (JP); Mitsuko Ishihara, Setagaya (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 1097 days.

(21) Appl. No.: 17/692,857

(22) Filed: Mar. 11, 2022

(65) Prior Publication Data

US 2022/0195401 A1 Jun. 23, 2022

Related U.S. Application Data

(63) Continuation of application No. PCT/JP2021/010622, filed on Mar. 16, 2021.

(30) Foreign Application Priority Data

Jun. 10, 2020 (JP) ................................ 2020-101013

(51) Int. Cl.
*C12N 9/12* (2006.01)

(52) U.S. Cl.
CPC ................................ *C12N 9/1241* (2013.01)

(58) Field of Classification Search
CPC ................................ C12N 9/1241
See application file for complete search history.

(56) References Cited

U.S. PATENT DOCUMENTS 6,773,914 B1 * 8/2004 Handler ................ A01K 67/68 536/23.1
2010/0240133 A1 9/2010 Brivanlou et al.
2013/0160152 A1 6/2013 Ostertag et al.
2017/0058285 A1 * 3/2017 Yokoi ................ C12N 15/8209
2017/0226531 A1 8/2017 Craig
2018/0163213 A1 * 6/2018 Aneja ................ C12N 15/52
2019/0062724 A1 * 2/2019 Hsu ................ C12N 15/113
2019/0323018 A1 10/2019 Minshull et al.
2019/0359971 A1 11/2019 Zhang et al.

FOREIGN PATENT DOCUMENTS

CN 101215577 A 7/2008
CN 105481984 A 4/2016
JP 2007-259775 A 10/2007
JP 2018-518183 A 7/2018
JP 2018-518454 A 7/2018
JP 2019-518478 A 7/2018
JP 2019-518454 A 7/2019
JP 2019-524072 A 9/2019
WO WO 2020250181 * 12/2002
WO WO-2016/161410 A2 10/2016
WO WO 2016/205711 A1 12/2016
WO WO 2017/201476 A1 11/2017
WO WO 2017/223538 A1 12/2017

OTHER PUBLICATIONS

Machine Translation, English, CN105481984, Apr. 13, 2016.*
Japanese Office Action issued Sep. 17, 2024 in Japanese Patent Application No. 2023 72885 (with unedited computer-generated English translation), citing document 15 therein, 6 pages.
Written Opinion issued Oct. 5, 2021 in PCT/JP2021/010622 filed on Mar. 16, 2021, citing documents AC-AD & AY-AZ therein, 5 pages.
Caracciolo et al., "Role of the interaction between large T antigen and Rb family members in the oncogenicity of JC virus", Oncogene, vol. 25, No. 38, 2006, pp. 5294-5301, DOI: 10.1038/sj.onc.1209681.
Li et al., "piggyBac transposase tools for genome engineering", Proceedings of the National Academy of Sciences, vol. 110, No. 25, 2013, pp. E2279-E2287, DOI: 10.1073/pnas.1305987110.
Yusa et al., "A hyperactive piggyBac transposase for mammalian applications", Proceedings of the National Academy of Sciences, vol. 108, No. 4, 2011, pp. 1531-1536, DOI: 10.1073/pnas.1008322108.
Hong et al., "A Nucleolus-Predominant piggyBac Transposase, NP-mPB, Mediates Elevated Transposition Efficiency in Mammalian Cells", PLOS ONE, vol. 9, No. 2, 2014, e89396, pp. 1-12, DOI: 10.1371/journal.pone.0089396.
Keith et al., "Analysis of the piggyBac transposase reveals a functional nuclear targeting signal in the 94 c-terminal residues" BMC Molecular Biology, vol. 9: 72, 2008, pp. 1-13, DOI: 10.1186/1471-2199-9-72.

* cited by examiner

*Primary Examiner* — Suzanne M Noakes
(74) *Attorney, Agent, or Firm* — Oblon, McClelland, Maier & Neustadt, L.L.P.

(57) ABSTRACT

According to one embodiment, a modified piggyBac transposase polypeptide includes a piggyBac transposase amino acid sequence and a nuclear localization signal amino acid sequence.

20 Claims, 6 Drawing Sheets

Specification includes a Sequence Listing.

MODIFIED PIGGYBAC TRANSPOSASE POLYPEPTIDE, POLYNUCLEOTIDE ENCODING THEM, INTRODUCING CARRIER, KIT, METHOD OF INCORPORATING TARGET SEQUENCE INTO CELL GENOME, AND METHOD OF PRODUCING CELL

CROSS-REFERENCE TO RELATED APPLICATIONS

This application is a Continuation Application of PCT Application No. PCT/JP2021/010622, filed Mar. 16, 2021 and based upon and claiming the benefit of priority from Japanese Patent Application No. 2020-101013, filed Jun. 10, 2020, the entire contents of all of which are incorporated herein by reference.

REFERENCE TO A SEQUENCE LISTING

In accordance with 37 CFR § 1.831-1.835 and 37 CFR § 1.823 (b) (1), the specification makes reference to a Sequence Listing submitted electronically as a .txt file named "REPLACEMENT Oct. 19, 2025". This .txt file was generated on Oct. 19, 2025, and is 32,200 bytes in size. The entire contents of the Sequence Listing are hereby incorporated herein by reference.

FIELD

Embodiments described herein relate generally to a modified piggyBac transposase polypeptide, a polynucleotide encoding them, an introducing carrier, a kit, a method of incorporating a target sequence into a cell genome, and a method of producing a cell.

BACKGROUND

The transposon method is attracting attention as a method for incorporating a target sequence into a cell genome. In the transposon method, an enzyme called transposase is used. Transposase has a function of excising a target sequence having recognition sequences at both ends and inserting the target sequence into the genome. For example, the moth-derived piggyBac transposase is known.

The technique of incorporating a target sequence into a cell genome has been applied in various fields such as genetically modified cells, production of genetically modified animals, gene therapy, and regenerative medicine. Therefore, there is an increasing demand for the efficiency and simplification of the incorporation technique.

DETAILED DESCRIPTION

Figure 1:
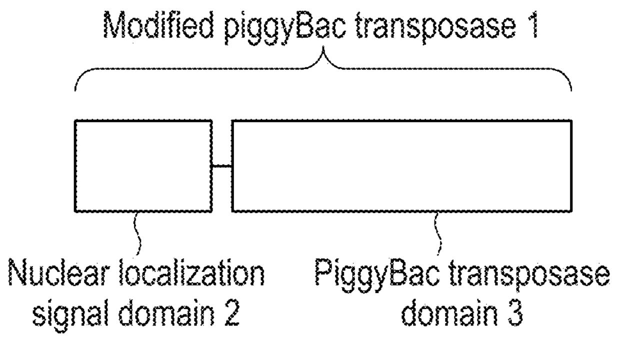
FIG. 1 is a diagram illustrating an example of a modified piggyBac transposase of a first embodiment.

In general, according to one embodiment, the modified piggyBac transposase polypeptide includes a piggyBac transposase amino acid sequence and a nuclear localization signal amino acid sequence.

Hereinafter, embodiments will be described with reference to the accompanying drawings. Note that, in each of the embodiments, substantially the same components may be designated by the same reference numerals, and the description thereof may be partially omitted. The drawings are schematic, and the relationship between the thickness of each part and the plane dimensions, the ratio of the thickness of each part, and the like may differ from the actual ones.

According to the embodiment, a modified piggyBac transposase is provided. When referred to herein simply as "modified piggyBac transposase", it refers to the form of a modified piggyBac transposase polypeptide. According to a further embodiment, a polynucleotide encoding the modified piggyBac transposase may also be provided.

The modified piggyBac transposase of the embodiment can be used, for example, to incorporate a target sequence into a cell genome. Therefore, according to a further embodiment, there are also provided a method of incorporating a target sequence into a cell genome using a modified piggyBac transposase, a kit used therein, and a method of producing a cell. Hereinafter, each of the embodiments will be described.

First Embodiment

Modified PiggyBac Transposase

A modified piggyBac transposase 1 of the first embodiment includes a nuclear localization signal domain 2 and a piggyBac transposase domain 3 as illustrated in FIG. 1. Hereinafter, the nuclear localization signal domain 2 is also referred to as "NLS domain", and the piggyBac transposase domain 3 is also referred to as "PB domain".

The PB domain 3 is a domain including the piggyBac transposase amino acid sequence. The piggyBac transposase refers to a transposase derived from *Trichoplushia ni*, which is a kind of moth, or a derivative thereof. As the PB domain 3, for example, the amino acid sequence of the wild-type piggyBac transposase shown in Table 1 (SEQ ID NO: 1) can be used.

TABLE 1

| Wild-type piggyBac transposase (SEQ ID NO: 1) | |
|---|---|
| MGSSLDDEHI LSALLQSDDE LVGEDSDSEI SDHVSEDDVQ SDTEEAFIDE VHEVQPTSSG | 60 |
| SEILDEQNVI EQPGSSLASN RILTLPQRTI RGKNKHCWST SKSTRRSRVS ALNIVRSQRG | 120 |
| PTRMCRNIYD PLLCFKLFFT DEIISEIVKW TNAEISLKRR ESMTGATFRD TNEDEIYAFF | 180 |

TABLE 1-continued

| Wild-type piggyBac transposase (SEQ ID NO: 1) | | | | | | |
|---|---|---|---|---|---|---|
| GILVMTAVRK | DNHMSTDDLF | DRSLSMVYVS | VMSRDRFDFL | IRCLRMDDKS | IRPTLRENDV | 240 |
| FTPVRKIWDL | FIHQCIQNYT | PGAHLTIDEQ | LLGFRGRCPF | RMYIPNKPSK | YGIKILMMCD | 300 |
| SGTKYMINGM | PYLGRGTQTN | GVPLGEYYVK | ELSKPVHGSC | RNITCDNWFT | SIPLAKNLLQ | 360 |
| EPYKLTIVGT | VRSNKREIPE | VLKNSRSRPV | GTSMFCFDGP | LTLVSYKPKP | AKMVYLLSSC | 420 |
| DEDASINEST | GKPQMVMYYN | QTKGGVDTLD | QMCSVMTCSR | KTNRWPMALL | YGMINIACIN | 480 |
| SFIIYSHNVS | SKGEKVQSRK | KFMRNLYMSL | TSSFMRKRLE | APTLKRYLRD | NISNILPNEV | 540 |
| PGTSDDSTEE | PVMKKRTYCT | YCPSKIRRKA | NASCKKCKKV | ICREHNIDMC | QSCF | 594 |

Alternatively, the sequence of the PB domain 3 is not limited to the above sequence, and for example, derivatives having mutations such as substitutions, additions, insertions, and deletions of amino acids included in the sequence shown in Table 1 can also be used. For example, it is preferable to use a derivative having 90% or more of amino acid sequence homology with the sequence shown in Table 1. It is also possible to use the sequence shown in Table 2 (SEQ ID NO: 2), which is a derivative of the wild-type piggyBac transposase. SEQ ID NO: 2 is preferable since it has underlined seven amino acid substitutions from SEQ ID NO: 1 and has a higher activity as the transposase.

TABLE 2

| Amino acid sequence-modified piggyBac transposase (SEQ ID NO: 2) | | | | | | |
|---|---|---|---|---|---|---|
| MGSSLDDEHI | LSALLQSDDE | LVGEDSDSE**V** | SDHVSEDDVQ | SDTEEAFIDE | VHEVQPTSSG | 60 |
| SEILDEQNVI | EQPGSSLASN | RILTLPQRTI | RGKNKHCWST | SK**P**TRRSRVS | ALNIVRSQRG | 120 |
| PTRMCRNIYD | PLLCFKLFFT | DEIISEIVKW | TNAEISLKRR | ESMT**S**ATFRD | TNEDEIYAFF | 180 |
| GILVMTAVRK | DNHMSTDDLF | DRSLSMVYVS | VMSRDRFDFL | IRCLRMDDKS | IRPTLRENDV | 240 |
| FTPVRKIWDL | FIHQCIQNYT | PGAHLTIDEQ | LLGFRGRCPF | R**V**YIPNKPSK | YGIKILMMCD | 300 |
| SGTKYMINGM | PYLGRGTQTN | GVPLGEYYVK | ELSKPVHGSC | RNITCDNWFT | SIPLAKNLLQ | 360 |
| EPYKLTIVGT | VRSNKREIPE | VLKNSRSRPV | GTSMFCFDGP | LTLVSYKPKP | AKMVYLLSSC | 420 |
| DEDASINEST | GKPQMVMYYN | QTKGGVDTLD | QMCSVMTCSR | KTNRWPMALL | YGMINIACIN | 480 |
| SFIIYSHNVS | SKGEKVQSRK | KFMRNLYM**G**L | TSSFMRKRLE | APTLKRYLRD | NISNILP**K**EV | 540 |
| PGTSDDSTEE | PVMKKRTYCT | YCPSKIRRKA | **S**ASCKKCKKV | ICREHNIDMC | QSCF | 594 |

The NLS domain 2 is a domain including the nuclear localization signal (NLS) amino acid sequence. Any known NLS polypeptide can be used as the NLS domain 2. The NLS may be a classical NLS or a non-classical NLS.

As the classical NLS, for example, NLS of the large T antigen protein of simian virus 40 (SV40) shown in Table 3 (SEQ ID NO: 3) can be used.

TABLE 3

| NLS of large T antigen protein of SV40 (SEQ ID NO: 3) | |
|---|---|
| KKKRKV | 6 |

Alternatively, as the typical NLS, nucleoplasmin, NLS of sex-determining region Y (SRY), or the like can be used.

As the non-classical NLS, for example, the trans-activator of transcription (TAT) protein (SEQ ID NO: 4) of human immunodeficiency virus (HIV) shown in Table 4 can be used.

TABLE 4

| TAT protein of HIV (SEQ ID NO: 4) | |
|---|---|
| GRKKRRQRRR | 10 |

Alternatively, as the non-classical NLS, NLS of Borna disease virus (BDV) p10, phospholipid scramblase 1 (PLSCR1), Ty1 integrase, HIV-1 Rev, human T-cell leukemia type 1 (HTLV-1) Rex, Ste12, Pho4 or Yap1, or the like can be used.

As the NLS domain 2, one of the above NLSs may be used singly, or a plurality of NLSs of the same or different types may be linked and used. For example, the classical NLS and the non-classical NLS may be linked and used as the NLS domain 2. As the NLS domain, it is preferable to use a sequence in which the TAT protein of HIV and the NLS of SV40 large T antigen protein are linked in this order from the N-terminus.

For example, the NLS domain 2 and the PB domain 3 are preferably linked in this order from the N-terminal side, but they also can be linked in the order the PB domain 3, the NLS domain 2.

As used in the present specification, the term "linked" means that respective domains are bound in a state in which the domains can perform their functions. In addition, the term "linked" includes both a state of being directly bound and a state of being bound through a different sequence. The different sequence may be an amino acid or a polypeptide that does not adversely affect the function of each domain. For example, the different sequence is preferably a sequence around the domain in the genome of the living organism from which each domain is derived, a GGGGS sequence or a GS sequence, or a sequence obtained by repeating these sequences 1 to 5 times.

Polynucleotide Encoding Modified PiggyBac Transposase

According to a further embodiment, a polynucleotide encoding the modified piggyBac transposase is provided. The polynucleotide is, for example, a polymer including deoxyribonucleotides, ribonucleotides, or other nucleotides capable of constituting a base sequence. The polynucleotides may be, for example, genomic DNA, cDNA, artificially synthesized DNA, genomic RNA, or artificially synthesized RNA, which is single-stranded, double-stranded or triple-stranded, or a nucleic acid analog in which the site or terminus thereof is chemically modified. The polynucleotide can include a plurality of types of nucleotides, and can contain a bridged nucleic acid (BNA), a locked nucleic acid (LNA), a peptide nucleic acid (PNA), and the like.

The polynucleotide of the embodiment encodes the modified piggyBac transposase 1, and includes, for example, at least a region (base sequence) encoding the NLS domain 2 and a region encoding the PB domain 3.

Here, the term "encoding" means including information, that is, a base sequence that can transcribe and/or translate and express a target polypeptide. The information is specified, for example, by codons corresponding to respective amino acids that constitute the polypeptide.

An example in which the polynucleotide is RNA will be described below. For example, this RNA is introduced into a cell and functions as messenger RNA (mRNA). The RNA is translated by the intracellular protein synthesis function to supply the modified piggyBac transposase 1 into the cell.

Preferably, the RNA sequence is codon-optimized according to the species of the cell to be introduced, and used. The term "codon-optimized" refers to changing the codon for each amino acid constituting a peptide to a codon that is used with high frequency in the species. However, the term "codon-optimized" does not necessarily mean that codons of 100% of amino acids in the amino acid sequence of the polypeptide are changed, but that at least one codon among codons corresponding to amino acids is changed. However, it is preferable that 50% or more of the codons are changed.

For example, in the case of using human cells, it is preferable to perform codon optimization for humans. Hereinafter, the codons that are used with high frequency in humans and are preferable for codon optimization for humans are shown for each amino acid.

Alanine (A): GCU or GCC is used with high frequency and preferred, but GCC is used with the highest frequency and more preferred.

Cysteine (C): UGC or UGU is used with high frequency and preferred, but UGC is used with the highest frequency and more preferred.

Aspartic acid (D): GAC or GAU is used with high frequency and preferred, but GAC is used with the highest frequency and more preferred.

Glutamic acid (E): GAA or GAG is used with high frequency and preferred, but GAG is used with the highest frequency and more preferred.

Phenylalanine (F): UUC or UUU is used with high frequency and preferred, but UUC is used with the highest frequency and more preferred.

Glycine (G): GGA or GGC is used with high frequency and preferred, but GGC is used with the highest frequency and more preferred.

Histidine (H): CAC or CAU is used with high frequency and preferred, but CAC is used with the highest frequency and more preferred.

Isoleucine (I): AUC or AUU is used with high frequency and preferred, but AUC is used with the highest frequency and more preferred.

Lysine (K): AAA or AAG is used with high frequency and preferred, but AAG is used with the highest frequency and more preferred.

Leucine (L): CUC or CUG is used with high frequency and preferred, but CUG is used with the highest frequency and more preferred.

Methionine (M): The codon used is one type (AUG) and does not need to be changed.

Asparagine (N): AAC or AAU is used with high frequency and preferred, but AAC is used with the highest frequency and more preferred.

Proline (P): CCC or CCU is used with high frequency and preferred, but CCC is used with the highest frequency and more preferred.

Glutamine (Q): CAA or CAG is used with high frequency and preferred, but CAG is used with the highest frequency and more preferred.

Arginine (R): AGA or AGG is used with high frequency and their usage frequencies are equal, and both AGA and AGG are preferred.

Serine (S): AGC, UCC or UCU is used with high frequency and preferred, but AGC is used with the highest frequency and more preferred. UCC is used with the second highest frequency and preferred.

Threonine (T): ACA or ACC is used with high frequency and preferred, but ACC is used with the highest frequency and more preferred.

Valine (V): GUC or GUG is used with high frequency and preferred, but GUG is used with the highest frequency and more preferred.

Tryptophan (W): The codon used is one type (UGG) and does not need to be changed.

Tyrosine (Y): UAC or UAU is used with high frequency and preferred, but UAC is used with the highest frequency and more preferred.

Stop codon: UGA is used with the highest frequency and more preferred.

Here, A is adenine, U is uracil, C is cytosine, and G is guanine.

However, when the content of the codon used with the highest frequency is too high, the translation efficiency may rather decrease due to reasons such as depletion of tRNA for the codon or a too high GC content of the polypeptide. Therefore, it is preferable to include the second most frequently used codon at a certain ratio.

As the region encoding the PB domain 3, for example, a sequence known as piggyBac transposase mRNA can be used. Alternatively, it is preferable to use a sequence which is obtained by codon-optimizing this mRNA sequence as described above.

As the region encoding the NLS domain 2, a known RNA sequence encoding any of the above desired NLS domains 2 may be used. It is also preferable that the NLS domain 2 is codon-optimized according to the species of the cell to be used.

The RNA of the embodiment may be in the form of pre-RNA before RNA processing or in the form of mature RNA after processing. The RNA of the embodiment may contain additional sequences in addition to the region encoding each domain. Examples of the additional sequences include start codon, stop codon, 5' untranslated region (5' UTR), 3' untranslated region (3' UTR), 5' end leader sequence, internal ribosome entry site (IRES), 2A sequences such as P2A and T2A, transcription termination sequences, poly (A) sequences, or the like.

The RNA of the embodiment is preferably modified to have degradation resistance. For example, the modification may be a known modification that prevents RNA from being degraded by RNase or the like. Examples of the modification include the use and introduction of naturally modified or unnatural nucleotides into RNA, the use and addition of unnatural sequences, or the addition of natural or unnatural CAP structures, or the addition of poly (A) sequences, or the like.

Examples of the naturally modified nucleotides include pseudouridine, 5-methylcytidine, 1-methyladenosine, and the like. Examples of the unnatural nucleotides include BNA, LNA, PNA, and the like.

Examples of the unnatural sequences include an artificially created non-naturally occurring base sequence, e.g., a random base sequence or a hybrid sequence of natural or unnatural amino acids and a nucleic acid, and the like. The unnatural sequence is preferably added, for example, to the terminus of RNA.

Examples of the natural CAP structure include CAP0 (m7GpppN), CAP1 (m7GpppNm), and the like. Examples of the unnatural CAP structure include an anti-reverse cap analog (ARCA), LNA-guanosine, and the like. The unnatural CAP structure is preferably added, for example, to the 5' terminus of RNA.

RNA of the embodiment can be synthesized from the DNA sequence of the modified piggyBac transposase described below by using an in vitro transcription method or the like. In vitro transcription can be performed using a commercially available kit, e.g., CUGA (registered trademark) 7 kit or the like. Alternatively, RNA may be artificially synthesized directly.

Subsequently, an example in which the polynucleotide is DNA will be described. The DNA is transcribed and translated, for example, after being introduced into the cell, and supplies the modified piggyBac transposase 1 into a cell.

The DNA of the first embodiment contains at least a region (base sequence) encoding each domain (the NLS domain 2 and the PB domain 3) of the desirable modified piggyBac transposase 1. As the region encoding each domain, for example, a sequence of known DNA encoding the polypeptide of each domain can be used. The region encoding each domain may include a sequence in which uracil (U) of the RNA sequence is changed to thymine (T), or a complementary sequence (cDNA) thereof.

As the region encoding the PB domain 3, for example, a wild-type DNA sequence (Table 5, SEQ ID NO: 5) encoding the amino acid sequence of SEQ ID NO: 1 can be used.

TABLE 5

Wild-type DNA sequence encoding PB domain of SEQ ID NO: 1 (SEQ ID NO: 5)

| | | | | | | |
|---|---|---|---|---|---|---|
| ATGGGTAGTT | CTTTAGACGA | TGAGCATATC | CTCTCTGCTC | TTCTGCAAAG | CGATGACGAG | 60 |
| CTTGTTGGTG | AGGATTCTGA | CAGTGAAATA | TCAGATCACG | TAAGTGAAGA | TGACGTCCAG | 120 |
| AGCGATACAG | AAGAAGCGTT | TATAGATGAG | GTACATGAAG | TGCAGCCAAC | GTCAAGCGGT | 180 |
| AGTGAAATAT | TAGACGAACA | AAATGTTATT | GAACAACCAG | GTTCTTCATT | GGCTTCTAAC | 240 |
| AGAATCTTGA | CCTTGCCACA | GAGGACTATT | AGAGGTAAGA | ATAAACATTG | TTGGTCAACT | 300 |
| TCAAAGTCCA | CGAGGCGTAG | CCGAGTCTCT | GCACTGAACA | TTGTCAGATC | TCAAAGAGGT | 360 |
| CCGACGCGTA | TGTGCCGCAA | TATATATGAC | CCACTTTTAT | GCTTCAAACT | ATTTTTTACT | 420 |
| GATGAGATAA | TTTCGGAAAT | TGTAAAATGG | ACAAATGCTG | AGATATCATT | GAAACGTCGG | 480 |
| GAATCTATGA | CAGGTGCTAC | ATTTCGTGAC | ACGAATGAAG | ATGAAATCTA | TGCTTTCTTT | 540 |
| GGTATTCTGG | TAATGACAGC | AGTGAGAAAA | GATAACCACA | TGTCCACAGA | TGACCTCTTT | 600 |
| GATCGATCTT | TGTCAATGGT | GTACGTCTCT | GTAATGAGTC | GTGATCGTTT | TGATTTTTTG | 660 |
| ATACGATGTC | TTAGAATGGA | TGACAAAAGT | ATACGGCCCA | CACTTCGAGA | AAACGATGTA | 720 |
| TTTACTCCTG | TTAGAAAAAT | ATGGGATCTC | TTTATCCATC | AGTGCATACA | AAATTACACT | 780 |
| CCAGGGGCTC | ATTTGACCAT | AGATGAACAG | TTACTTGGTT | TTAGAGGACG | GTGTCCGTTT | 840 |
| AGGATGTATA | TCCCAAACAA | GCCAAGTAAG | TATGGAATAA | AAATCCTCAT | GATGTGTGAC | 900 |
| AGTGGTACGA | AGTATATGAT | AAATGGAATG | CCTTATTTGG | GAAGAGGAAC | ACAGACCAAC | 960 |
| GGAGTACCAC | TCGGTGAATA | CTACGTGAAG | GAGTTATCAA | AGCCTGTGCA | CGGTAGTTGT | 1020 |
| CGTAATATTA | CGTGTGACAA | TTGGTTCACC | TCAATCCCTT | TGGCAAAAAA | CTTACTACAA | 1080 |
| GAACCGTATA | AGTTAACCAT | TGTGGGAACC | GTGCGATCAA | ACAAACGCGA | GATACCGGAA | 1140 |

TABLE 5-continued

| Wild-type DNA sequence encoding PB domain of SEQ ID NO: 1 (SEQ ID NO: 5) |
|---|
| GTACTGAAAA ACAGTCGCTC CAGGCCAGTG GGAACATCGA TGTTTTGTTT TGACGGACCC 1200 |
| CTTACTCTCG TCTCATATAA ACCGAAGCCA GCTAAGATGG TATACTTATT ATCATCTTGT 1260 |
| GATGAGGATG CTTCTATCAA CGAAAGTACC GGTAAACCGC AAATGGTTAT GTATTATAAT 1320 |
| CAAACTAAAG GCGGAGTGGA CACGCTAGAC CAAATGTGTT CTGTGATGAC CTGCAGTAGG 1380 |
| AAGACGAATA GGTGGCCTAT GGCATTATTG TACGGAATGA TAAACATTGC CTGCATAAAT 1440 |
| TCTTTTATTA TATACAGCCA TAATGTCAGT AGCAAGGGAG AAAAGGTTCA AAGTCGCAAA 1500 |
| AAATTTATGA GAAACCTTTA CATGAGCCTG ACGTCATCGT TTATGCGTAA GCGTTTAGAA 1560 |
| GCTCCTACTT TGAAGAGATA TTTGCGCGAT AATATCTCTA ATATTTTGCC AAATGAAGTG 1620 |
| CCTGGTACAT CAGATGACAG TACTGAAGAG CCAGTAATGA AAAAACGTAC TTACTGTACT 1680 |
| TACTGCCCCT CTAAAATAAG GCGAAAGGCA AATGCATCGT GCAAAAAATG CAAAAAAGTT 1740 |
| ATTTGTCGAG AGCATAATAT TGATATGTGC CAAAGTTGTT TCTGA 1785 |

When used in human cells, the region encoding the PB domain 3 is preferably, for example, a sequence obtained using a triplet selected to provide codon-optimized RNA for humans as described above. The DNA sequence is codon-optimized using a triplet in which the U of the preferred codon corresponding to each of the amino acids described above is changed to T or a complementary sequence thereof. For example, it is preferable to use the sequence shown in Table 6 (SEQ ID NO: 6) as the DNA sequence obtained by codon optimization of the PB domain 3 of SEQ ID NO: 1.

TABLE 6

| DNA sequence codon-optimized for humans that encodes PB domain of SEQ ID NO: 1 (SEQ ID NO: 6) |
|---|
| ATGGGCTCCT CCCTCGATGA CGAGCACATT CTGTCCGCTC TGCTGCAGTC CGACGATGAG 60 |
| CTGGTCGGAG AAGACAGCGA TAGCGAGATC AGCGACCACG TCTCCGAGGA CGACGTCCAA 120 |
| AGCGACACAG AGGAGGCCTT TATCGACGAG GTCCATGAAG TGCAGCCCAC ATCCAGCGGC 180 |
| AGCGAGATTC TGGACGAGCA GAACGTGATC GAACAGCCCG GCAGCTCCCT CGCCAGCAAT 240 |
| AGAATTCTGA CACTGCCCCA GAGAACCATT AGAGGCAAGA ACAAGCACTG TTGGAGCACC 300 |
| AGCAAGAGCA CAAGAAGATC CAGAGTCAGC GCCCTCAACA TTGTGAGAAG CCAGAGGGGC 360 |
| CCTACAAGAA TGTGTAGAAA CATCTATGAC CCTCTGCTGT GTTTCAAGCT GTTCTTCACC 420 |
| GACGAGATCA TCAGCGAGAT CGTGAAGTGG ACCAACGCTG AGATCTCTCT GAAGAGGAGA 480 |
| GAAAGCATGA CCGGCGCCAC CTTTAGGGAC ACCAACGAGG ACGAAATCTA TGCTTTTTTT 540 |
| GGAATTCTGG TGATGACAGC CGTGAGGAAA GACAACCACA TGTCCACAGA TGATCTGTTT 600 |
| GATAGATCTC TGTCCATGGT GTATGTGAGC GTCATGTCCA GAGATAGATT CGATTTCCTC 660 |
| ATTAGATGTC TGAGGATGGA CGATAAGTCC ATCAGACCCA CACTGAGAGA GAACGACGTC 720 |
| TTTACCCCCG TGAGAAAAAT CTGGGACCTC TTCATCCACC AGTGCATCCA AAATTATACA 780 |
| CCCGGCGCTC ACCTCACCAT CGACGAGCAG CTCCTCGGCT TCAGAGGAAG ATGCCCCTTT 840 |
| AGAATGTACA TTCCCAACAA GCCCTCCAAG TACGGCATCA AGATCCTCAT GATGTGTGAC 900 |
| AGCGGCACCA AGTACATGAT CAACGGCATG CCCTATCTGG GAAGAGGCAC CCAGACCAAC 960 |
| GGAGTGCCCC TCGGCGAATA TTACGTGAAG GAACTGAGCA AACCCGTGCA CGGCAGCTGC 1020 |
| AGAAATATTA CATGCGATAA CTGGTTCACC AGCATCCCTC TGGCCAAAAA TCTGCTGCAA 1080 |
| GAGCCTTACA AGCTCACAAT CGTGGGAACC GTGAGGAGCA ACAAGAGGGA GATTCCCGAG 1140 |
| GTGCTCAAAA ACTCTAGATC TAGACCCGTG GGAACCTCCA TGTTCTGTTT CGACGGCCCT 1200 |
| CTGACACTCG TCTCCTATAA GCCCAAGCCC GCCAAGATGG TGTATCTGCT CAGCAGCTGC 1260 |

TABLE 6-continued

| DNA sequence codon-optimized for humans that encodes PB domain of SEQ ID NO: 1 (SEQ ID NO: 6) |
|---|
| GACGAAGACG CCAGCATCAA TGAATCCACC GGCAAGCCCC AGATGGTCAT GTACTACAAC 1320 |
| CAGACCAAGG GAGGCGTCGA TACACTGGAC CAGATGTGTT CCGTCATGAC ATGCTCTAGA 1380 |
| AAGACCAATA GATGGCCCAT GGCTCTGCTG TACGGCATGA TCAACATCGC TTGCATTAAC 1440 |
| TCCTTTATCA TTTACTCCCA TAACGTCAGC TCCAAGGGCG AGAAGGTGCA GAGCAGAAAG 1500 |
| AAATTCATGA GAAATCTGTA CATGAGCCTC ACCAGCAGCT TCATGAGAAA GAGGCTGGAG 1560 |
| GCCCCCACAC TGAAAAGATA TCTGAGAGAT AATATCTCCA ACATTCTGCC TAACGAGGTC 1620 |
| CCCGGCACAA GCGATGATAG CACAGAGGAG CCCGTGATGA AGAAGAGAAC ATACTGCACA 1680 |
| TACTGCCCCA GCAAGATTAG AAGGAAGGCC AACGCCAGCT GCAAGAAGTG CAAGAAGGTC 1740 |
| ATCTGCAGAG AGCACAACAT CGACATGTGC CAGAGCTGTT TTTGA 1785 |

Further, as the DNA sequence for humans obtained by codon optimization of the PB domain 3 of SEQ ID NO: 2, for example, the sequence shown in Table 7 (SEQ ID NO: 7) is preferably used.

TABLE 7

| DNA sequence codon-optimized for humans that encodes PB domain of SEQ ID NO: 2 (SEQ ID NO: 7) |
|---|
| ATGGGCAGCA GCCTGGACGA CGAGCACATC CTGAGCGCCC TGCTGCAGAG CGACGACGAG 60 |
| CTGGTCGGCG AGGACAGCGA CAGCGAGGTG AGCGACCACG TGAGCGAGGA CGACGTGCAG 120 |
| TCCGACACCG AGGAGGCCTT CATCGACGAG GTGCACGAGG TGCAGCCTAC CAGCAGCGGC 180 |
| TCCGAGATCC TGGACGAGCA GAACGTGATC GAGCAGCCCG GCAGCTCCCT GGCCAGCAAC 240 |
| AGGATCCTGA CCCTGCCCCA GAGGACCATC AGGGGCAAGA ACAAGCACTG CTGGTCCACC 300 |
| TCCAAGCCCA CCAGGCGGAG CAGGGTGTCC GCCCTGAACA TCGTGAGAAG CCAGAGGGGC 360 |
| CCCACCAGGA TGTGCAGGAA CATCTACGAC CCCCTGCTGT GCTTCAAGCT GTTCTTCACC 420 |
| GACGAGATCA TCAGCGAGAT CGTGAAGTGG ACCAACGCCG AGATCAGCCT GAAGAGGCGG 480 |
| GAGAGCATGA CCTCCGCCAC CTTCAGGGAC ACCAACGAGG ACGAGATCTA CGCCTTCTTC 540 |
| GGCATCCTGG TGATGACCGC CGTGAGGAAG GACAACCACA TGAGCACCGA CGACCTGTTC 600 |
| GACAGATCCC TGAGCATGGT GTACGTGAGC GTGATGAGCA GGGACAGATT CGACTTCCTG 660 |
| ATCAGATGCC TGAGGATGGA CGACAAGAGC ATCAGGCCCA CCCTGCGGGA GAACGACGTG 720 |
| TTCACCCCCG TGAGAAAGAT CTGGGACCTG TTCATCCACC AGTGCATCCA GAACTACACC 780 |
| CCTGGCGCCC ACCTGACCAT CGACGAGCAG CTGCTGGGCT TCAGGGGCAG GTGCCCCTTC 840 |
| AGGGTCTATA TCCCCAACAA GCCCAGCAAG TACGGCATCA AGATCCTGAT GATGTGCGAC 900 |
| AGCGGCACCA AGTACATGAT CAACGGCATG CCCTACCTGG GCAGGGGCAC CCAGACCAAC 960 |
| GGCGTGCCCC TGGGCGAGTA CTACGTGAAG GAGCTGTCCA AGCCCGTCCA CGGCAGCTGC 1020 |
| AGAAACATCA CCTGCGACAA CTGGTTCACC AGCATCCCCC TGGCCAAGAA CCTGCTGCAG 1080 |
| GAGCCCTACA AGCTGACCAT CGTGGGCACC GTGAGAAGCA ACAAGAGAGA GATCCCCGAG 1140 |
| GTCCTGAAGA ACAGCAGGTC CAGGCCCGTG GGCACCAGCA TGTTCTGCTT CGACGGCCCC 1200 |
| CTGACCCTGG TGTCCTACAA GCCCAAGCCC GCCAAGATGG TGTACCTGCT GTCCAGCTGC 1260 |
| GACGAGGACG CCAGCATCAA CGAGAGCACC GGCAAGCCCC AGATGGTGAT GTACTACAAC 1320 |
| CAGACCAAGG GCGGCGTGGA CACCCTGGAC CAGATGTGCA GCGTGATGAC CTGCAGCAGA 1380 |

TABLE 7-continued

| DNA sequence codon-optimized for humans that encodes PB domain of SEQ ID NO: 2 (SEQ ID NO: 7) | |
|---|---|
| AAGACCAACA GGTGGCCCAT GGCCCTGCTG TACGGCATGA TCAACATCGC CTGCATCAAC | 1440 |
| AGCTTCATCA TCTACAGCCA CAACGTGAGC AGCAAGGGCG AGAAGGTGCA GAGCCGGAAA | 1500 |
| AAGTTCATGC GGAACCTGTA CATGGGCCTG ACCTCCAGCT TCATGAGGAA GAGGCTGGAG | 1560 |
| GCCCCCACCC TGAAGAGATA CCTGAGGGAC AACATCAGCA ACATCCTGCC CAAAGAGGTG | 1620 |
| CCCGGCACCA GCGACGACAG CACCGAGGAG CCCGTGATGA AGAAGAGGAC CTACTGCACC | 1680 |
| TACTGTCCCA GCAAGATCAG AAGAAAGGCC AGCGCCAGCT GCAAGAAGTG TAAGAAGGTC | 1740 |
| ATCTGCCGGG AGCACAACAT CGACATGTGC CAGAGCTGTT TCTGA | 1785 |

When the NLS of SV40 large T antigen of SEQ ID NO: 3 is used as the NLS domain 2, the DNA sequence (SEQ ID NO: 8) shown in Table 8 below can be used as the region encoding the NLS domain 2.

TABLE 8

| DNA sequence of NLS of large T antigen protein of SV40 (SEQ ID NO: 8) | |
|---|---|
| AAGAAGAAGA CAAAGGTC | 18 |

When the TAT protein of HIV (SEQ ID NO: 4) is used as the NLS domain 2, the DNA sequence (SEQ ID NO: 9) shown in Table 9 below can be used as the region encoding the NLS domain 2.

TABLE 9

| DNA sequence of TAT protein of HIV (SEQ ID NO: 9) | |
|---|---|
| GGCAGAAAGA AGAGAAGACA GAGAAGAAGA | 30 |

Further, in the case of using the NLS domain 2 obtained by linking the TAT protein of HIV to the NLS of SV40 large T antigen, the DNA sequence (SEQ ID NO: 10) shown in Table 10 below can be used.

TABLE 10

| DNA sequence of TAT protein of HIV + NLS of large T antigen protein of SV40 (SEQ ID NO: 10) | |
|---|---|
| GGCAGAAAGA AGAGAAGACA GAGAAGAAGA CCCCCCGCCG GCACCAGCGT GAGCCTGAAG | 60 |
| AAGAAGAGAA AGGTGCCCCC CGCC | 84 |

It is also possible to use the sequence in which nucleotides contained in the base sequences shown in Tables 5 to 10 have mutations such as substitutions, additions, insertions, and deletions. For example, when such mutations are present, it is preferable to use the sequence having 90% or more of homology with the amino acid sequence encoded by the sequences shown in Tables 5 to 10.

The DNA of the embodiment is preferably used in the configuration of a piggyBac transposase expression unit in which a promoter sequence is further linked to the 5' terminus of the DNA and a transcription termination sequence is linked to the 3' terminus. As the promoter sequence, an early enhancer/promoter of cytomegalovirus (CMV), a promoter of simian virus 40 (SV40), or the like can be used. As the transcription termination sequence, the transcription termination sequence of bovine growth hormone (BGH) gene or the transcription termination sequence of simian virus 40 (SV40) can be used. The expression unit may be single-stranded or double-stranded, and may be linear or circular. The termini of the DNA may be labeled or modified with functional groups. Further, the expression unit may be incorporated into a known plasmid vector or viral vector and the resulting expression unit may be used.

Figure 2:
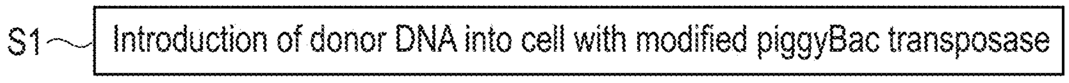
FIG. 2 is a flowchart illustrating an example of a method of incorporating a target sequence into a cell genome of the embodiment.

Method of Incorporating Target Sequence into Genome of Cell and Method of Producing Cell Hereinafter, the method of incorporating a target sequence into a cell genome using the modified piggyBac transposase of the first embodiment will be described. As illustrated in FIG. 2, the method of incorporating a target sequence into a cell genome includes introducing donor DNA into a cell with the modified piggyBac transposase 1 (S1: introduction step).

Figure 3:
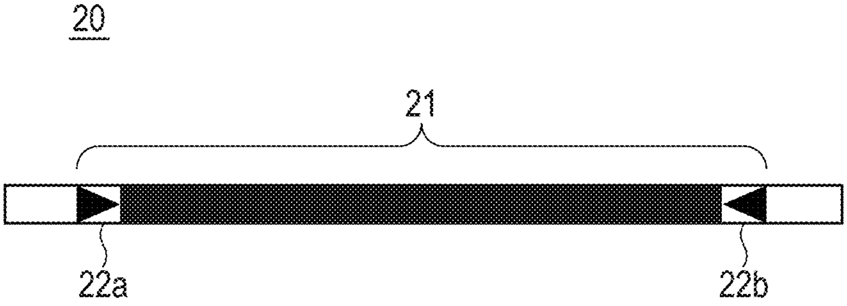
FIG. 3 is a diagram illustrating an example of donor DNA of the embodiment.

First, donor DNA will be described. As illustrated in FIG. 3, a donor DNA 20 contains a target sequence 21. The donor DNA 20 is, for example, double-stranded DNA, and may be linear or circular. For example, the donor DNA 20 may be a plasmid or viral vector in which the target sequence 21 is incorporated.

The target sequence 21 is a base sequence of DNA incorporated into the cell genome, and is selected according to the purpose of performing the present method. The target sequence 21 includes, for example, a base sequence encoding a specific gene or a part of a gene, a gene expression cassette containing a promoter sequence, a specific gene, and a transcription termination sequence, or a natural or unnatural base sequence that is not a gene. Alternatively, the target sequence 21 may contain a base sequence encoding one to several amino acids, a sequence including three to several dozens of nucleotides, and the like.

The target sequence 21 contains a first transposase recognition sequence 22*a* and a second transposase recognition sequence 22*b* at both ends thereof, respectively. The first transposase recognition sequence 22*a* and the second transposase recognition sequence 22*b* are sequences by which the transposase recognizes the position of the target sequence 21. The first transposase recognition sequence 22*a* and the second transposase recognition sequence 22*b* are sequences, also referred to as "inverted repeat sequences (IRs)" containing identical inverted sequences.

The region excluding the first transposase recognition sequence 22*a* and the second transposase recognition sequence 22*b* of the target sequence 21 has, for example, a length of about 3 to about 20000 bases.

The term "introducing the modified piggyBac transposase 1 into a cell" includes when introducing the modified piggyBac transposase 1 in the form of a polypeptide and when introducing the modified piggyBac transposase 1 in the form of RNA or DNA to express the modified piggyBac transposase 1 in a cell.

An example of the process by which the target sequence 21 is introduced into the cell genome when the modified piggyBac transposase 1 is incorporated in the form of RNA will be described with reference to FIG. 4. First, as illustrated in part (a) of FIG. 4, when the donor DNA 20 and an RNA 30 of the modified piggyBac transposase 1 are introduced into a cell 40, the modified piggyBac transposase 1 ("PB" in the figure) is expressed from the RNA 30 by the protein synthesis function of the cell 40 as illustrated in part (b) of FIG. 4. As illustrated in part (c) of FIG. 4, the donor DNA 20 and the modified piggyBac transposase 1 can translocate into a nucleus 41.

Figure 4:
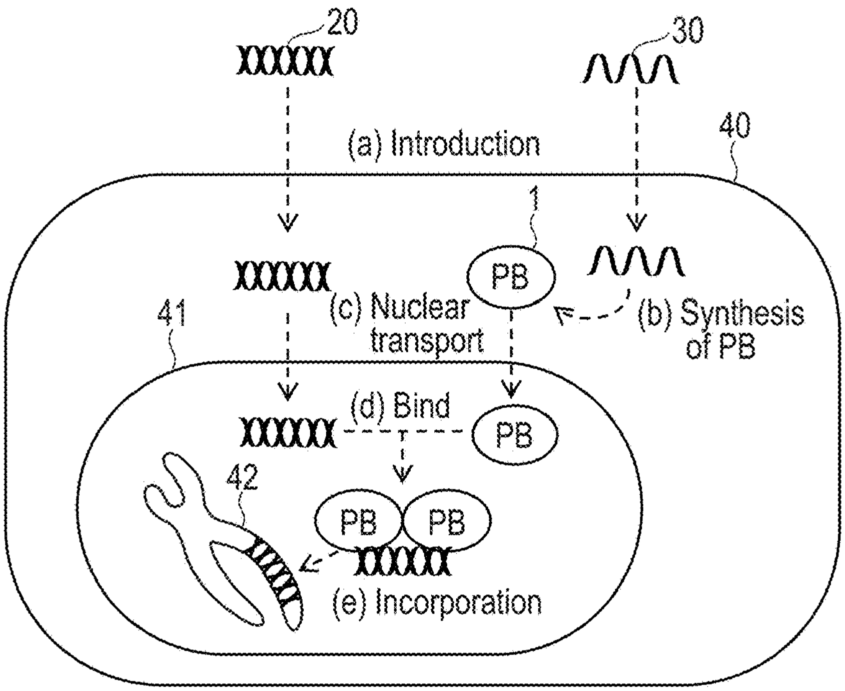
FIG. 4 is also a schematic diagram illustrating an example of a process of incorporating a target sequence into a cell genome using the modified piggyBac transposase of the embodiment.

Then, the modified piggyBac transposase 1 binds to the donor DNA 20 in the nucleus (part (d) of FIG. 4). For example, two modified piggyBac transposases 1 can bind to the first transposase recognition sequence 22*a* and the second transposase recognition sequence 22*b* of the donor DNA 20, respectively. The modified piggyBac transposase 1 then excises the target sequence 21 of the donor DNA 20, and the target sequence 21 is incorporated into a genome 42 of the cell 40 as illustrated in part (e) of FIG. 4.

In the case of using the DNA of the modified piggyBac transposase 1, after the DNA is introduced into the cell 40, the DNA is transcribed and translated, and the modified piggyBac transposase 1 is expressed in a similar manner to part (b) of FIG. 4, followed by the subsequent process. When the modified piggyBac transposase 1 is introduced in the form of a polypeptide, it can translocate directly into the nucleus 41.

Since the modified piggyBac transposase 1 of the embodiment has the NLS domain 2, the translocation efficiency into the nucleus 41 is further improved, and the target sequence 21 can be incorporated more efficiently.

Further, when the region encoding the PB domain 3 of the RNA 30 is codon-optimized according to the species of the cell, the modified piggyBac transposase 1 can be expressed more efficiently and the incorporation efficiency can be further improved.

The form in which the modified piggyBac transposase 1 is introduced may be suitably selected according to the type of introduction method, availability, and the like. However, it is preferable to use the form of RNA. In that case, since the transcription step can be omitted as compared to the case of using the form of DNA, the modified piggyBac transposase 1 can be expressed more quickly and with high efficiency, and the incorporation efficiency can be improved. Further, the modified piggyBac transposase 1 in the form of RNA is not incorporated into the genome 42 of the cell 40, so this is convenient.

The introduction step (S1) can be performed using any of the known methods used for introducing a polypeptide or polynucleotide into a cell. For example, it is preferable to use a liposome method, a lipofection method, an electroporation method, a sonoporation method, a magnetofection method, or the like. As the introduction method, a suitable method is selected according to the type of the cell 40, the type of the target sequence 21, the use of the cell 40 after introduction, and the like.

The liposome method is a more preferable introduction method, and refers to a method in which the donor DNA 20 and the modified piggyBac transposase 1 or a polynucleotide encoding the modified piggyBac transposase 1 are encapsulated in liposomes (lipid particles) and brought into contact with the cell 40. The embodiment of the liposome method will be described in detail later.

The lipofection method refers to a method in which, for example, the donor DNA 20 and the modified piggyBac transposase 1 in the form of a complex with lipids are brought into contact with the cell 40.

It is preferable to introduce about 1 to 100 molecules of each of the donor DNA 20 and the RNA 30.

The cell 40 is preferably an in vitro cell. The in vitro cell 40 can be, for example, an isolated cell, a cultured cell or tissue, or an established cell line. The cell 40 is preferably a mammalian cell, more preferably a human cell.

A target cell in which the target sequence 21 is incorporated into the genome can be produced by the method of incorporating a target sequence into a cell genome of the embodiment using the in vitro cell 40. Therefore, according to the embodiment, there is provided a method of producing a cell that includes the introduction step (S1). The method of producing a cell may further include a step of culturing the cell 40 under conditions suitable for survival after the introduction step (S1). Additionally, the method may further include a step of screening a target cell into which the target sequence 21 is incorporated after culturing.

In the method of producing a cell of the embodiment, the incorporation efficiency is improved by the modified piggyBac transposase 1, so that it is possible to produce the target cell more efficiently. The method of producing a cell of the embodiment can be used, for example, for the production of a target-cell containing pharmaceutical composition, the production of a substance-producing cell, or the like, without limitation.

Alternatively, the cell 40 may be an in vivo cell. In this case, the introduction step (S1) can be performed by administering the donor DNA 20 and the modified piggyBac transposase 1 to the living body. The administration can be performed, for example, by intravenous, subcutaneous, intramuscular, intraarterial, epidural, cerebrospinal, thoracic, intraperitoneal or local intralesional injection or infusion.

Liposome Method

Hereinafter, an example of an embodiment of the liposome method using RNA of the modified piggyBac transposase 1 will be described. However, in the liposome method, it is not always necessary to use the modified piggyBac transposase 1 in the form of RNA. The form of DNA and other forms: the form of a polynucleotide or the form of a polypeptide may be used. However, the form of a polynucleotide is preferred.

Figure 5:
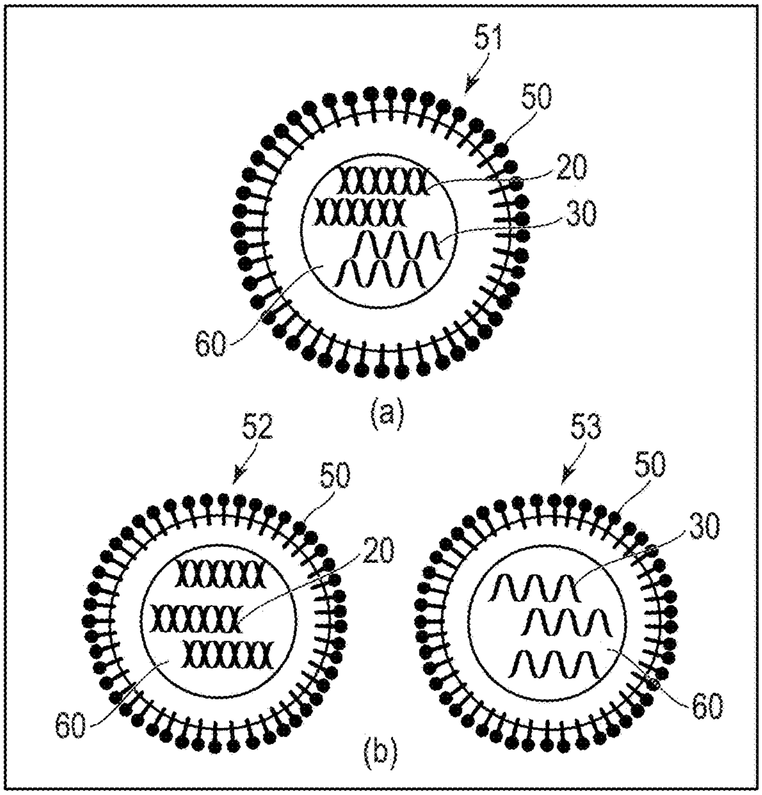
FIG. 5 is a cross-sectional view showing an example of each introducing carrier of the embodiment.

Part (a) of FIG. 5 illustrates an example of an introducing carrier 51 obtained by encapsulating the donor DNA 20 and the RNA 30 of the modified piggyBac transposase 1 in lipid particles 50. The introducing carrier 51 is brought into contact with the cell 40, whereby the lipid particles 50 and the cell membrane can be fused by, for example, endocytosis, and the donor DNA 20 and the RNA 30 can be released into the cell 40.

Part (b) of FIG. 5 illustrates an example of introducing carriers 52 and 53 obtained by encapsulating the donor DNA 20 and the RNA 30 in separate lipid particles 50, respectively. The introducing carriers 52 and 53 are used together. These introducing carriers 52 and 53 may be contacted with the cell 40 at the same time, or either one of them may be contacted first.

The lipid particle 50 is an approximately spherical hollow body including a lipid membrane obtained by arranging a plurality of lipid molecules by a non-covalent bond. The donor DNA 20 and/or the RNA 30 is encapsulated in a central lumen of the hollow body. The lipid particle 50 may be a lipid monolayer membrane or a lipid bilayer membrane. Further, the lipid particle 50 may include a single-layer membrane or a multi-layer membrane.

As the material of the lipid particle 50, the base lipids exemplified below can be used. As the base lipid, for example, a lipid that is the main component of the biological membrane can be used. The base lipid is a phospholipid or sphingolipid, such as diacylphosphatidylcholine, diacylphosphatidylethanolamine, ceramide, sphingomyelin, dihydrosphingomyelin, cephalin or cerebroside, or a combination thereof. The base lipid is easy to fuse with the cell membrane. Particularly, in the case of using diacylphosphatidylcholine and diacylphosphatidylethanolamine, the structure and particle size of the lipid particle 50 are easily controlled, and the base lipid is likely to be fused with the cell membrane, which is preferable. The hydrocarbon chain of the acyl group in the lipid preferably has a length of C10 to C20. This hydrocarbon chain may be a saturated hydrocarbon group or an unsaturated hydrocarbon group.

As the base lipid, it is preferable to use
1,2-dioleoyl-sn-glycero-3-phosphoethanolamine (DOPE),
1,2-stearoyl-sn-glycero-3-phosphoethanolamine (DSPE),
1,2-dipalmitoyl-sn-glycero-3-phosphatidylcholine (DPPC),
1-palmitoyl-2-oleoyl-sn-glycero-3-phosphatidylcholine (POPC),
1,2-di-O-octadecyl-3-trimethylammonium propane (DOTMA),
1,2-dioleoyl-3-dimethylammonium propane (DODAP),
1,2-dimyristoyl-3-dimethylammonium propane (14: 0 DAP),
1,2-dipalmitoyl-3-dimethylammonium propane (16: 0 DAP),
1,2-distearoyl-3-dimethylammonium propane (18: 0 DAP),
N-(4-carboxybenzyl)-N,N-dimethyl-2,3-bis(oleoyloxy)propan (DOBAQ),
1,2-dioleoyl-3-trimethylammonium propane (DOTAP),
1,2-dioleoyl-sn-glycero-3-phosphochlorine (DOPC),
1,2-dilinoleoyl-sn-glycero-3-phosphochlorine (DLPC),
1,2-dioleoyl-sn-glycero-3-phospho-L-serine (DOPS), or cholesterol,
or a combination of any of these base lipids. As the base lipid, it is particularly preferable to use a cationic lipid or a neutral lipid, and the acid dissociation constant of the lipid particle 50 can be adjusted by the content of the cationic lipid or the neutral lipid. It is preferable to use DOTAP as the cationic lipid, and it is preferable to use DOPE as the neutral lipid.

The base lipid may be contained in an amount close to 100% of the total lipid molecules contained in the lipid particle 50. Preferably, in addition to the base lipid, a first lipid compound and/or a second lipid compound as exemplified below are further contained. When these lipid compounds are contained, the base lipid is preferably contained in an amount of about 30% to about 80% (mole ratio) with respect to the total lipid molecules.

The first lipid compound is, for example, biodegradable. The first lipid compound can be represented by the formula Q-CHR2, wherein Q is a nitrogen-containing aliphatic group containing two or more tertiary nitrogen but containing no oxygen, and each R is independently an aliphatic group of C12 to C24 provided that at least one R has, in the main chain or side chain thereof, a linking group LR selected from the group consisting of —C(═O)—O—, —O—C(═O)—, —O—C(═O)—O—, —S—C(═O)—, —(═O)—S—, —C(═O)—NH—, and —NHC(═O)—.

When the lipid particle 50 contains the first lipid compound, the surface of the lipid particle 50 becomes non-cationic, because of which the obstacle in the cell introduction can be reduced and the introduction efficiency of the encapsulated substance can be increased.

For example, when lipid having structures represented by the following formulas is used as the first lipid compound, the introduction efficiency is more excellent, and this is preferred.

(1-01)

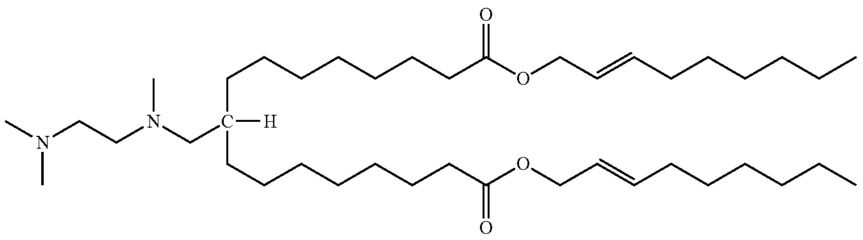

(1-02)

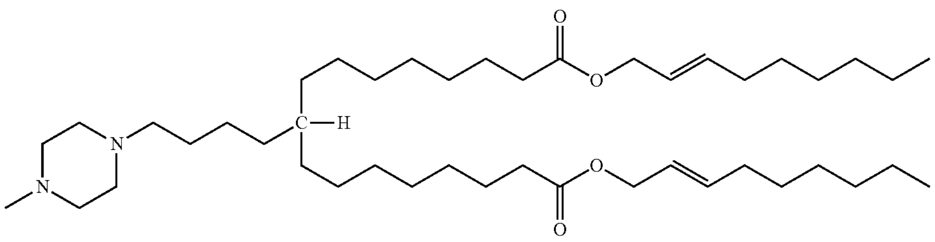

-continued
(1-03)
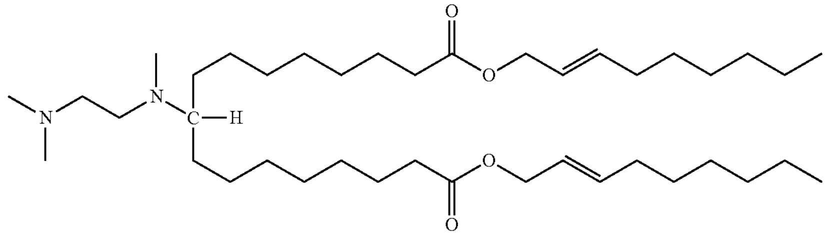
(1-04)
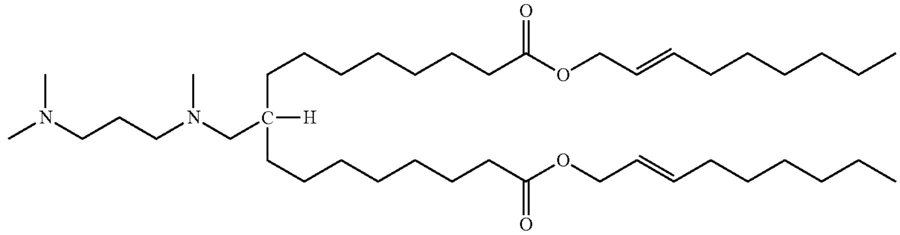
(1-05)
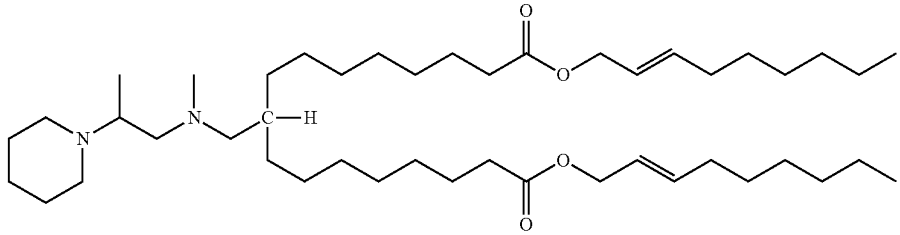
(1-06)
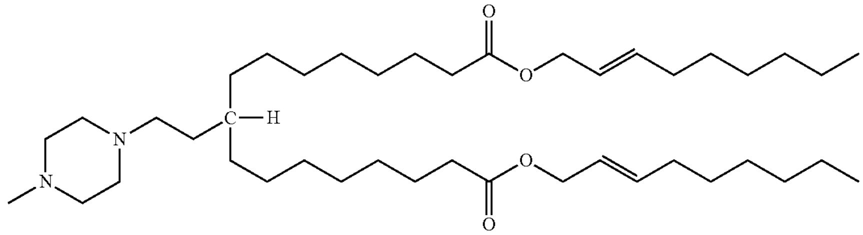
(1-07)
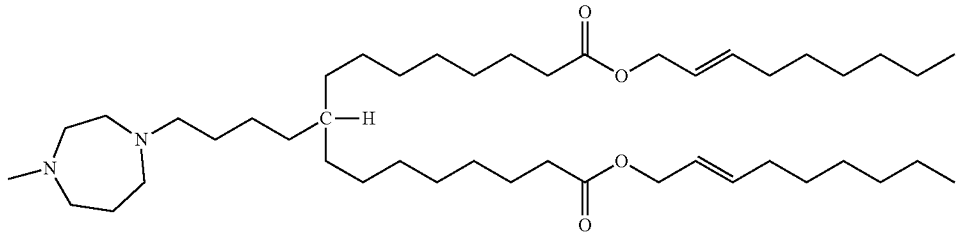
(1-08)
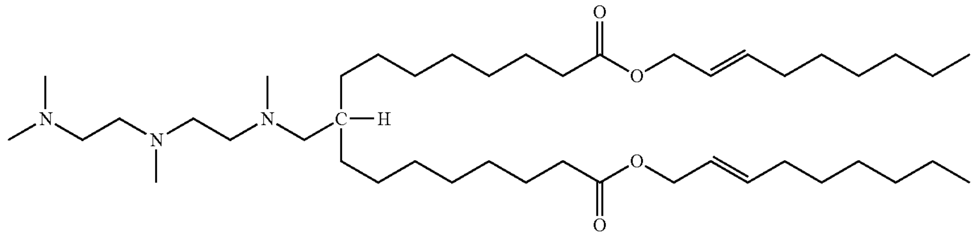

-continued
(1-09)
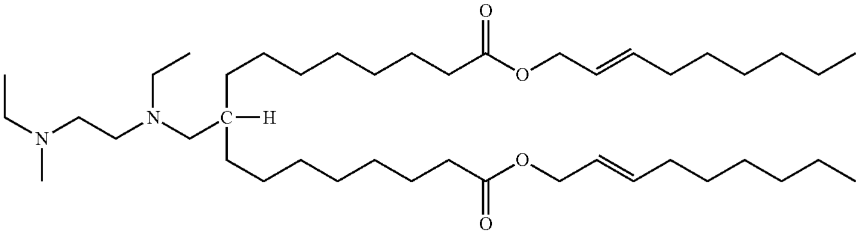
(1-10)
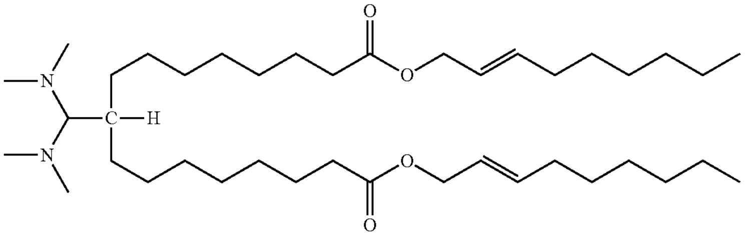
(1-11)
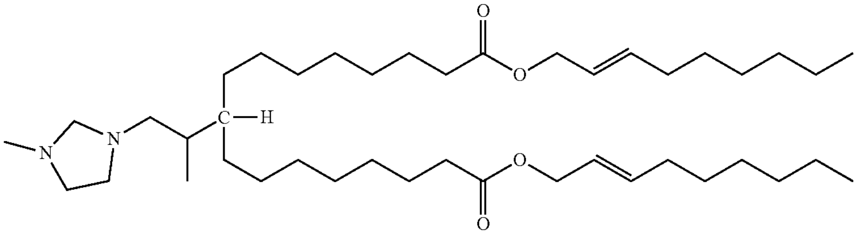
(1-12)
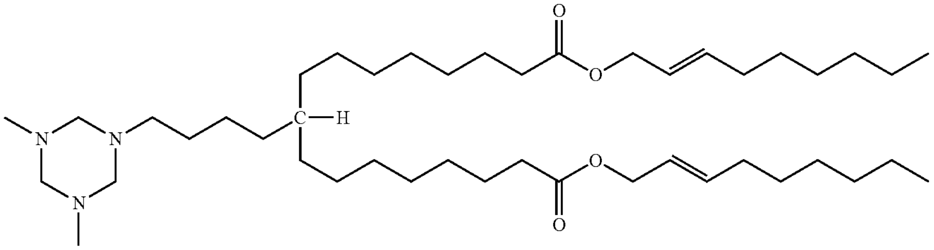
(1-13)
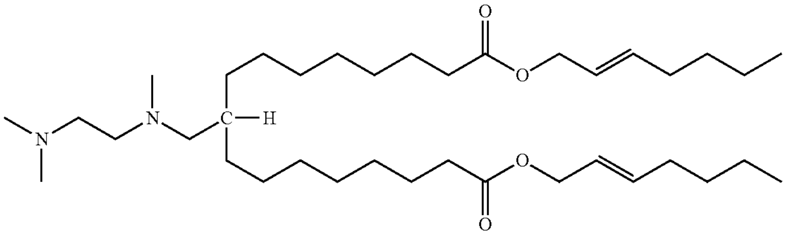
(1-14)
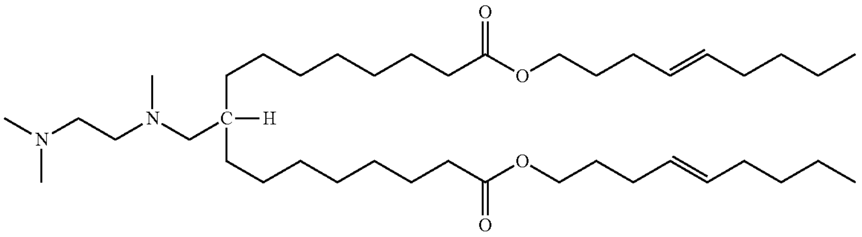

-continued
(1-15)
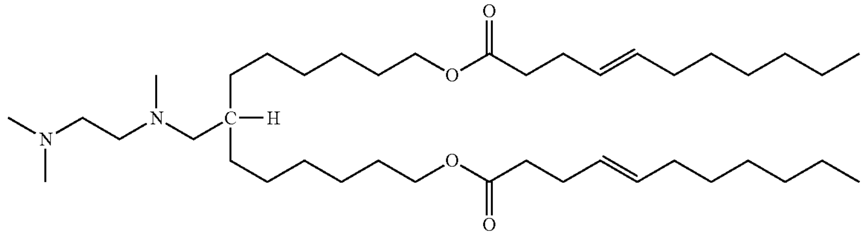
(1-16)
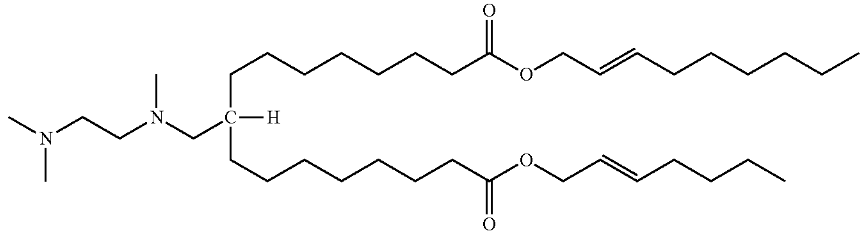
(1-17)
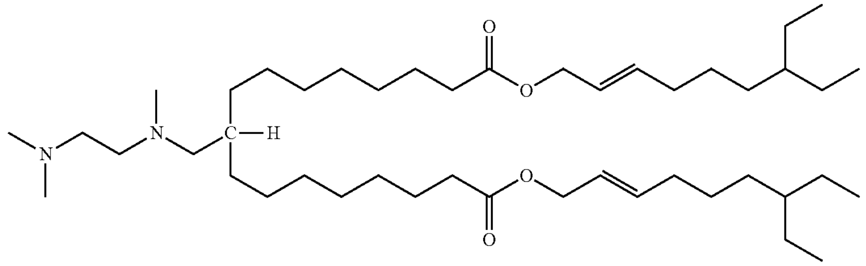
(1-18)
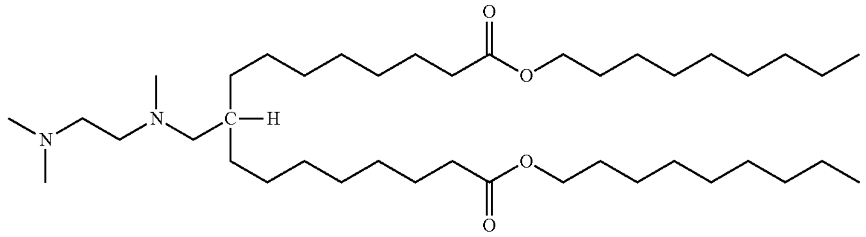
(1-19)
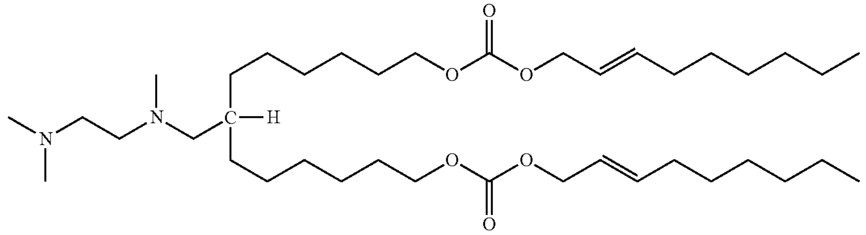
(1-20)
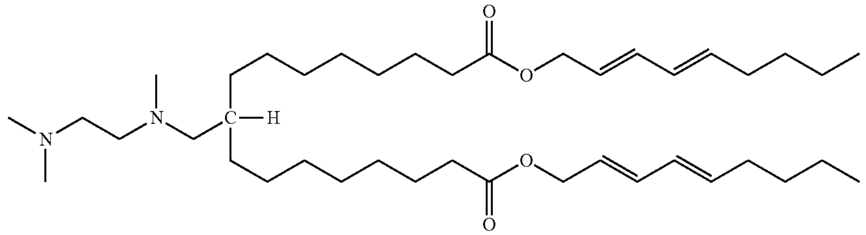

-continued (1-21)

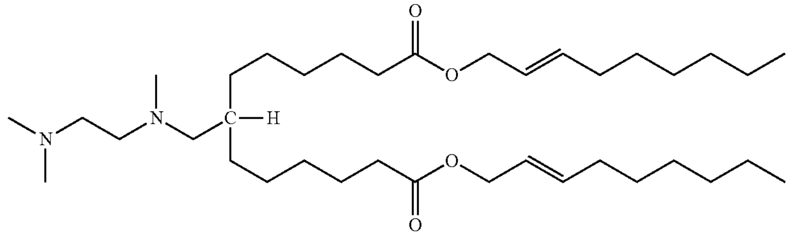

In particular, the lipid particle 50 preferably contains a lipid compound of Formula (1-01) and/or a lipid compound of Formula (1-02) as a constituent component thereof.

The second lipid compound is, for example, biodegradable. The second lipid compound can be represented by the formula P—[X—W—Y—W—Z]2.

(wherein P is an alkyleneoxy having one or more ether bonds in the main chain, each X is independently a divalent linking group having a tertiary amine structure, each W is independently a C1 to C6 alkylene, each Y is independently a divalent linking group selected from the group consisting of single bond, ether bond, carboxylic ester bond, thiocarboxylic ester bond, thioester bond, amide bond, carbamate bond, and urea bond, each W' is independently a single bond or a C1 to C6 alkylene, and each Z is independently a liposoluble vitamin residue, a sterol residue, or a C12 to C22 aliphatic hydrocarbon group.)

When the second lipid compound is contained, the amount of nucleic acid encapsulated in the lipid particle 50 may be large.

For example, when the second lipid compound having the following structures are used, the amount of nucleic acid encapsulated is more excellent, and this is preferred.

(2-01)

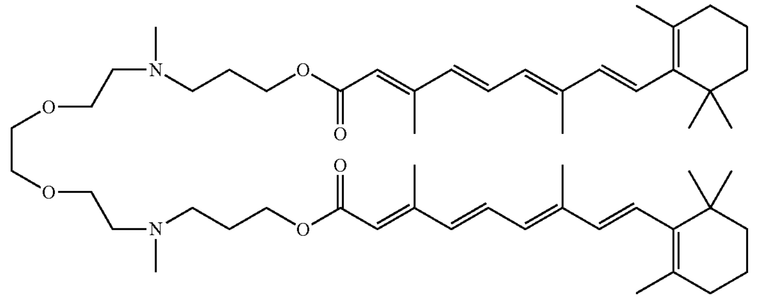

(2-02)

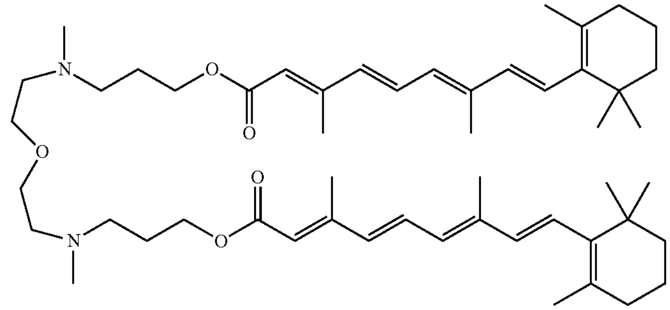

(2-03)

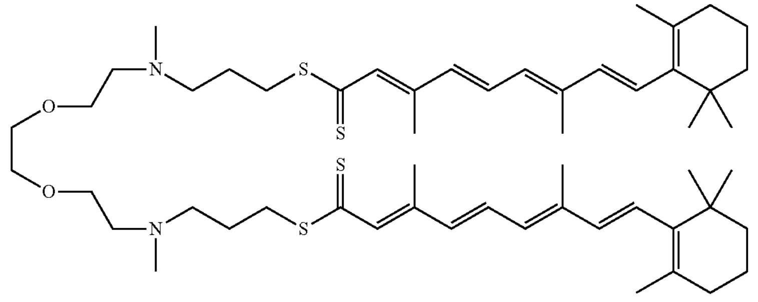

-continued
(2-04)
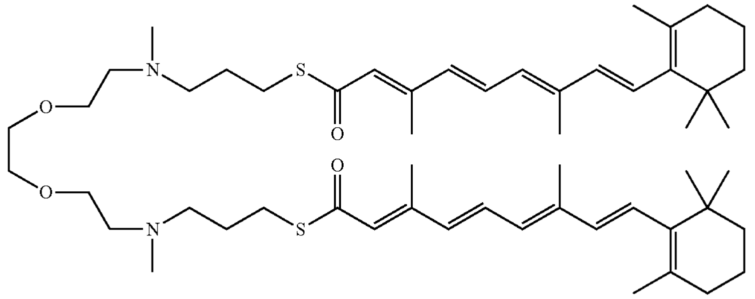
(2-05)
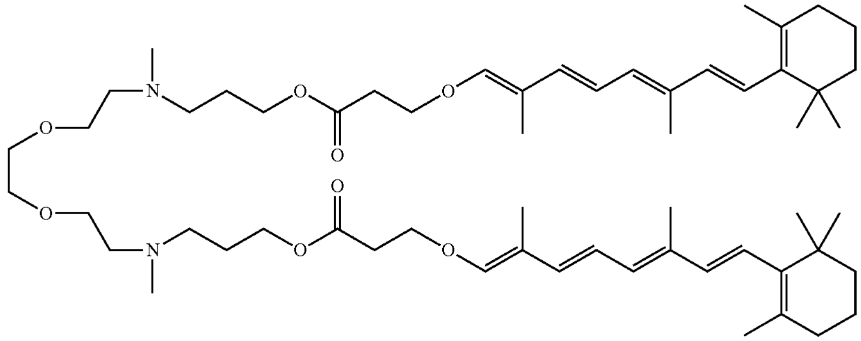
(2-06)
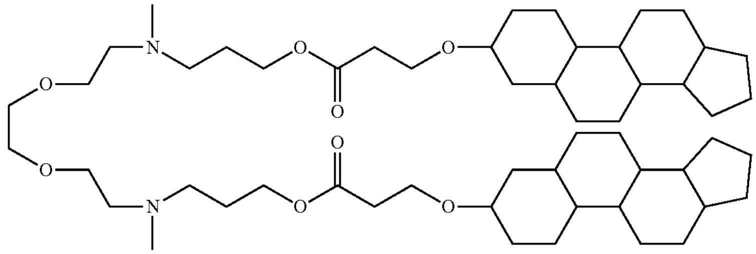
(2-07)
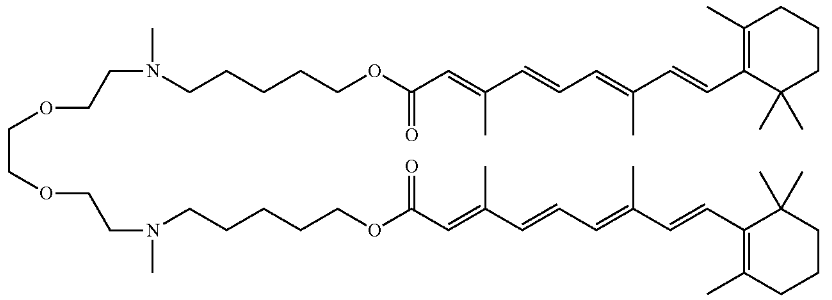
(2-08)
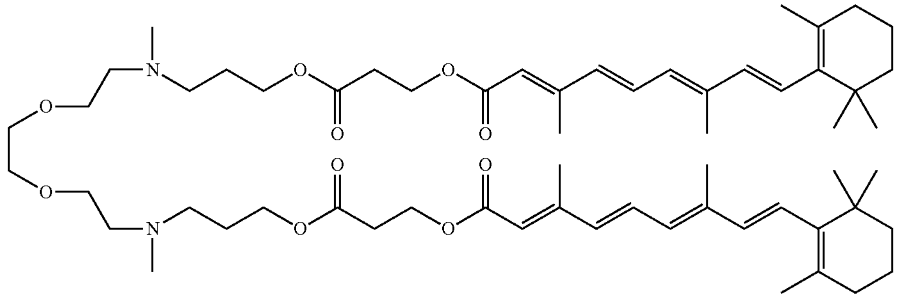

-continued
(2-09)
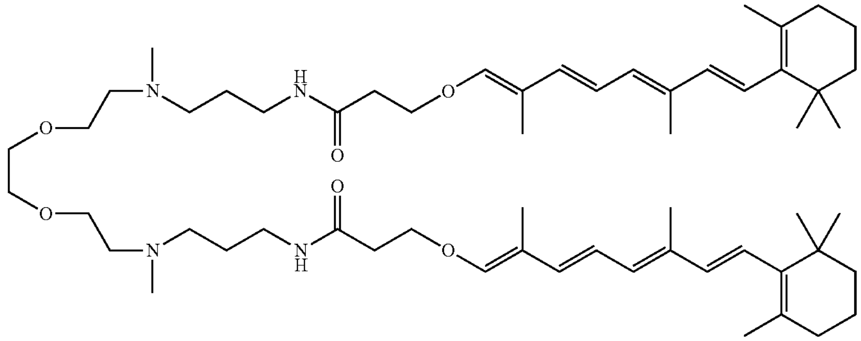
(2-10)
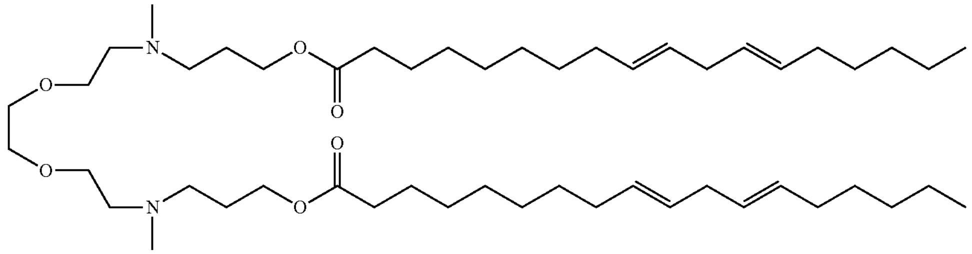
(2-11)
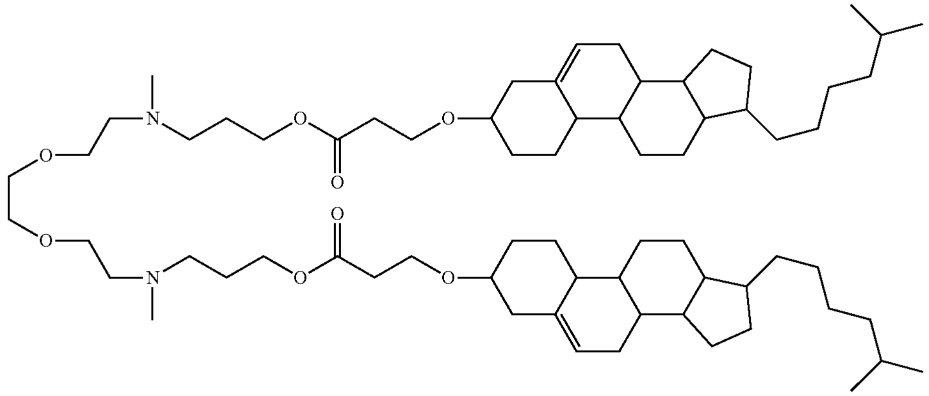
(2-12)
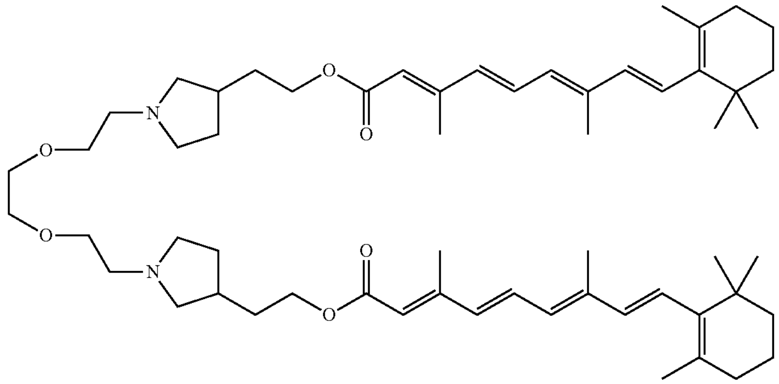

When the lipid particle 50 containing the first and second lipid compounds described above is used, it is possible to increase the encapsulation amount and increase the introduction efficiency. Moreover, the cell death of the introduced cells can be reduced. In particular, when the compounds of Formulas (1-01), (1-02) and/or (2-01) are used, the encapsulation amount and the introduction efficiency are particularly excellent, and this is preferred.

The first and second lipid compounds are preferably contained in an amount of about 20% to about 70% (mole ratio) with respect to the total materials of the lipid particle 50.

It is also preferable that the lipid particle 50 contains a lipid that prevents the lipid particle 50 from aggregating. For example, the lipid that prevents aggregation preferably further contains a PEG-modified lipid, such as polyethylene glycol (PEG) dimyristylglycerol (DMG-PEG), polyamide oligomer derived from ω-amino (oligoethyleneglycol) alkanoic acid monomers (U.S. Pat. No. 6,320,017 B), or monosialoganglioside. Such lipids are preferably contained in an amount of about 1% to about 5% (mole ratio) with respect to the total materials of the lipid particle 50.

The lipid particle 50 may contains lipids such as relatively low-toxic lipids for regulating toxicity; lipids having a functional group that binds a ligand to the lipid particle 50; and lipids for suppressing leakage of an encapsulated substance such as sterol (e.g., cholesterol). In particular, cholesterol is preferably contained.

The type and composition of the lipid used for the lipid particle 50 are suitably selected by taking into consideration the acid dissociation constant (pKa) of the lipid particle 50 to be targeted, the size of the lipid particle 50, the type of the encapsulated substance, the stability of the cells to be introduced, and the like. The acid dissociation constant (pKa) is preferably in a range of 6.5 to 8.0. When the acid dissociation constant is a value in this range, it is possible to increase the introduction efficiency.

For example, when the lipid particle 50 contains a compound of Formula (1-01) or Formula (1-02) and/or a compound of Formula (2-01), DOPE and/or DOTAP, cholesterol, and DMG-PEG, the encapsulation amount of nucleic acid and the introduction efficiency of nucleic acid are particularly excellent, and this is preferred.

Additional components may be encapsulated in an introducing carrier, if necessary. Examples of the additional components include pH adjusters, osmotic pressure regulators, gene activators or other therapeutic agents for T-cell tumor cells, other diagnostic agents, and the like. Examples of the pH regulators include organic acids such as a citric acid and a salt thereof. Examples of the osmotic pressure regulators include sugar, amino acids, and the like. The gene activators will be described later.

The introducing carrier can be produced, for example, by using a known method used for encapsulating small molecules in lipid particles, such as a Bangham method, an organic solvent extraction method, a surfactant removal method, or a freezing and thawing method. For example, a lipid mixture obtained by immersing the material of the lipid particles 50 in an organic solvent such as alcohol in a desired ratio and an aqueous buffer solution containing a component to be encapsulated are prepared, and the aqueous buffer solution is added to the lipid mixture. The resulting mixture is stirred and suspended to form an introducing carrier.

The donor DNA 20 and the RNA 30 may be encapsulated in a condensed state with a nucleic acid condensing peptide 60. The nucleic acid condensing peptide 60 is a peptide having a function of condensing nucleic acids into small particles. By using the nucleic acid condensing peptide 60, a large amount of nucleic acids can be encapsulated in the lipid particles 50, and the particle size of the lipid particles 50 can be reduced. Further, the amount of nucleic acids remaining outside the lipid particles 50 is reduced, thereby preventing aggregation of introducing carriers. As a result, the delivery efficiency of nucleic acids can be improved.

The preferred nucleic acid condensing peptide 60 is, for example, a peptide containing 45% or more of the total cationic amino acids. The more preferred nucleic acid condensing peptide 60 has a sequence RRRRRR (SEQ ID NO: 23) (first amino acid sequence) at one end and a sequence RQRQR (SEQ ID NO: 22) (second amino acid sequence) at the other end. Zero or one or more intermediate sequences of RRRRRR (SEQ ID NO: 23) or RQRQR (SEQ ID NO: 22) are contained between the first amino acid sequence and the second amino acid sequence. Further, two or more neutral amino acids are contained between two adjacent sequences of the first amino acid sequence, the second amino acid sequence, and the intermediate sequence. The neutral amino acids are, for example, G or Y. Alternatively, the other end may have the sequence RRRRRR (SEQ ID NO: 23) (first amino acid sequence) instead of the second amino acid sequence.

The above-described nucleic acid condensing peptides preferably has the following amino acid sequences:

```
                    (SEQ ID NO: 11)
RQRQRYYRQRQRGGRRRRRR;

                    (SEQ ID NO: 12)
RQRQRGGRRRRRR;
and

                    (SEQ ID NO: 13)
RRRRRRYYRQRQRGGRRRRRR.
```

Further, a nucleic acid condensing peptide having the following amino acid sequence can be used in combination with any of the above-described nucleic acid condensing peptides. This peptide can further condense a nucleic acid aggregate formed by condensation of the above-described nucleic acid condensing peptides.

```
                                        (SEQ ID NO: 14)
GNQSSNFGPMKGGNFGGRSSGPYGGGGQYFAKPRNQGGY (M9)
```

For example, the nucleic acid can be condensed by stirring and mixing the nucleic acid with the nucleic acid condensing peptide 60 before being encapsulated in the lipid particles 50. The donor DNA 20 and the RNA 30 may be condensed together or separately.

It is preferable to use the nucleic acid condensing peptide 60 because the effects described above are obtained. However, the nucleic acid condensing peptide 60 is not necessarily used depending on the type of nucleic acid used, the type of cell, and the like.

Kit

According to the embodiment, there is provided a kit used for incorporating the target sequence 21 into the cell genome. The kit includes at least one of the modified piggyBac transposases 1 or the polynucleotide encoding the modified piggyBac transposase 1.

For example, the modified piggyBac transposase 1 or the polynucleotide encoding the modified piggyBac transposase 1 may be provided as a composition contained in a suitable carrier. Alternatively, the modified piggyBac transposase 1 or the polynucleotide encoding the modified piggyBac transposase 1 may be provided in the form of the introducing carrier as the composition contained in a suitable carrier. Examples of the suitable carrier include water, saline such as physiological saline, glycine aqueous solutions or buffers, and the like.

The composition may be sterilized by common methods. Further, the composition may also be provided as a liquid or as a dry powder. For example, the powder composition can be used by dissolving in a suitable liquid.

The kit may further include substances that improve the storage stability of the composition. The substances that improve the storage stability are not limited, and examples thereof include glycoproteins such as albumin, lipoprotein, apolipoprotein, and globulin: pH adjusters, buffer agents, tension regulators, and the like; pharmaceutically acceptable and involved agents that bring the pharmaceutical composition closer to the physiological state, such as sodium acetate, sodium lactate, sodium chloride, potassium chloride, and calcium chloride; lipophilic free-radical quenchers that suppress free radical damage, such as α-tocopherol; and lipid protectants such as a water-soluble chelator such as ferrioxamine for suppressing peroxidation damage of lipids and improving storage stability. These substances may be contained in the composition or may be included in the kit separately from the composition.

The kit may further include the donor DNA 20, unless the kit includes an introducing carrier in which donor DNA is encapsulated.

Second Embodiment

According to the second embodiment, there is provided a modified piggyBac transposase that further includes a cell division promoting domain. As illustrated in of part (a) of FIG. 6, a modified piggyBac transposase 10 of the second embodiment further includes a cell division promoting domain 4 between, for example, a nuclear localization signal domain 2 and a piggyBac transposase domain 3.

The cell division promoting domain 4 includes an amino acid sequence of a peptide having a function of promoting cell division. As the cell division promoting domain 4, any known peptide known to have such a function can be used. For example, it is preferable to use a sequence having a region of the N-terminus of the SV40 large T antigen protein to 133 amino acids (SEQ ID NO: 15) as shown in Table 11. This sequence contains the J domain and the Rb family-binding motif.

TABLE 11

| Cell division promoting domain including J domain and Rb family-binding motif of SV40 large T antigen protein (SEQ ID NO: 15) | |
|---|---|
| DKVLNREESL QLMDLLGLER SAWGNIPLMR KAYLKKCKEF HPDKGGDEEK MKKMNTLYKK | 60 |
| MEDGVKYAHQ PDFGGFWDAT EIPTYGTDEW EQWWNAFNEE NLFCSEEMPS SDDEATADSQ | 120 |
| HSTPPKKKRK VE | 132 |

The cell division promoting domain 4 is not limited to the above, and it is possible to use, for example, a cell division promoting domain of a large T antigen protein of JC virus or BK virus belonging to human polyomavirus.

Figure 6:
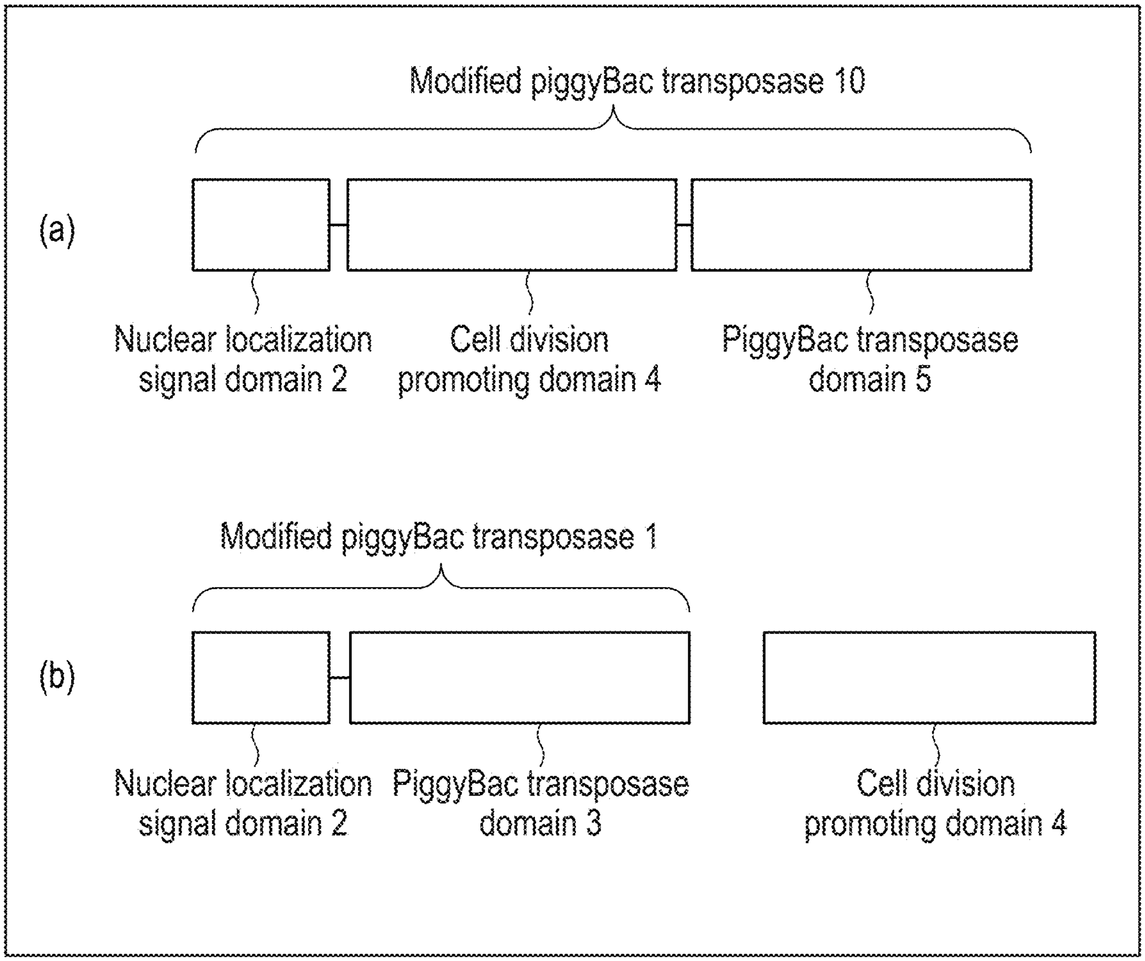
FIG. 6 is a diagram illustrating an example of a modified piggyBac transposase of a second embodiment.

When the cell division promoting domain 4 is included, the order in which each domain is linked is, for example, the NLS domain 2, the cell division promoting domain 4, and the PB domain 3 from the N-terminal side, as illustrated in part (a) of FIG. 6. However, the order of the domains is not limited to the above. For example, the cell division promoting domain 4, the NLS domain 2, and the PB domain 3 may be linked in this order from the N-terminal side. Alternatively, the domains may be linked in another order.

The second embodiment also provides a polynucleotide encoding the modified piggyBac transposase 10. When the amino acid sequence of SEQ ID NO: 15 is used as the cell division promoting domain 4, it is preferable to use, for example, the sequence shown in Table 12 (SEQ ID NO: 16) as the DNA sequence encoding the amino acid sequence.

TABLE 12

| DNA sequence encoding cell division promoting domain of SEQ ID NO: 15 (SEQ ID NO: 16) | |
|---|---|
| ATGGATAAAG TTTTAAACAG AGAGGAATCT TTGCAGCTAA TGGACCTTCT AGGTCTTGAA | 60 |
| AGGAGTGCCT GGGGGAATAT TCCTCTGATG AGAAAGGCAT ATTTAAAAAA ATGCAAGGAG | 120 |
| TTTCATCCTG ATAAAGGAGG AGATGAAGAA AAAATGAAGA AAATGAATAC TCTGTACAAG | 180 |
| AAAATGGAAG ATGGAGTAAA ATATGCTCAT CAACCTGACT TTGGAGGCTT CTGGGATGCA | 240 |

TABLE 12-continued

| DNA sequence encoding cell division promoting domain of SEQ ID NO: 15 (SEQ ID NO: 16) | |
|---|---|
| ACTGAGATTC CAACCTATGG AACTGATGAA TGGGAGCAGT GGTGGAATGC CTTTAATGAG | 300 |
| GAAAACCTGT TTTGCTCAGA AGAAATGCCA TCTAGTGATG ATGAGGCTAC TGCTGACTCT | 360 |
| CAACATTCTA CTCCTCCAAA AAAGAAGAGA AAGGTAGAA | 399 |

As the amino acid sequence or DNA sequence shown in Tables 11 and 12, the sequences having mutations such as substitutions, additions, insertions, and deletions can also be used. For example, when such mutations are present, it is preferable to use the sequence having a base sequence encoding an amino acid sequence having 90% or more of homology with the amino acid sequence encoded by the sequences shown in Tables 11 and 12.

The modified piggyBac transposase 10 of the second embodiment can also be provided as an introducing carrier similar to the introducing carrier described in the first embodiment. Further, similarly to the first embodiment, the modified piggyBac transposase 10 can be used in the method of incorporating a target sequence into a cell genome and the method of producing a cell.

However, when the modified piggyBac transposase 10 of the second embodiment is introduced into a cell 40, the division of the cell 40 may be temporarily facilitated because of the cell division promoting function of the cell division promoting domain 4. Nuclear membrane loss that occurs during cell division of the cell 40 can further facilitate the translocation of the modified piggyBac transposase 10 and a donor DNA 20 into a nucleus 41. Therefore, according to the modified piggyBac transposase 10 of the second embodiment, the incorporation efficiency of a target sequence 21 can be further improved.

According to a further embodiment, the cell division promoting domain 4 does not necessarily have to be included in the modified piggyBac transposase. As illustrated in part (b) of FIG. 6, the modified piggyBac transposase 1 of the first embodiment and a polypeptide containing the cell division promoting domain 4 separated from the modified piggyBac transposase 1 may be used together. At this time, the polypeptide containing the cell division promoting domain 4 may further contain the NLS domain 2.

EXAMPLES

An example of producing and using the modified piggyBac transposase of the embodiment will be described hereinbelow.

Example 1 Synthesis of DNA Sequence of Modified PiggyBac Transposase

Synthesis of PB Domain DNA Sequence

A DNA sequence of the gene of the wild-type piggyBac transposase (WtPB, SEQ ID NO: 1) (SEQ ID NO: 5) and a DNA sequence of human codon-optimized PB (HuPB) (SEQ ID NO: 6) in which the DNA sequence of SEQ ID NO: 5 was codon-optimized for humans were synthesized. In addition, a DNA sequence (SEQ ID NO: 7) of hyper-active PB (HyPB) having a modified amino acid sequence was synthesized.

Synthesis of NLS Domain DNA Sequence

As the NLS domain, the nuclear transport signal of the TAT protein of HIV (TAT NLS, SEQ ID NO: 4) and the nuclear transport signal of the SV40 large T antigen protein (SV40 NLS, SEQ ID NO: 3) were used. A DNA sequence of TAT NLS codon-optimized for humans (SEQ ID NO: 9), a DNA sequence of SV40 NLS codon-optimized for humans (SEQ ID NO: 8), and a DNA sequence in which TAT NLS and SV40 NLS were linked in this order via a linker sequence (TAT-SV40 NLS, SEQ ID NO: 10) were synthesized.

Synthesis of Cell Division Promoting Domain DNA Sequence

As the cell division promoting domain, the N-terminal 133-amino acid sequence containing the J domain and the Rb domain of the SV40 large T antigen protein (LT-J/Rb, SEQ ID NO: 15) was used. A DNA sequence (SEQ ID NO: 16) encoding the amino acid sequence of SEQ ID NO: 15 was synthesized.

Synthesis of DNA Sequence of Modified PiggyBac Transposase of First Embodiment There was produced T-HyPB (SEQ ID NO: 17) in which the DNA sequence of TAT NLS was added to an N-terminus of HyPB via a linker sequence, and TS-HyPB (SEQ ID NO: 18) in which a linker sequence was linked to TAT-SV40 NLS and added to an N-terminus of HyPB. These sequences are shown in Tables 13 and 14, respectively.

TABLE 13

| T-HyPB (SEQ ID NO: 17) | |
|---|---|
| ATGGGCGGCA GAAAGAAGAG AAGACAGAGA AGAAGACCCC CCGCCTCCTC CCTCGATGAC | 60 |
| GAGCACATTC TGTCCGCTCT GCTGCAGTCC GACGATGAGC TGGTCGGAGA AGACAGCGAT | 120 |
| AGCGAGATCA GCGACCACGT CTCCGAGGAC GACGTCCAAA GCGACACAGA GGAGGCCTTC | 180 |
| ATCGACGAGG TGCACGAGGT GCAGCCTACC AGCAGCGGCT CCGAGATCCT GGACGAGCAG | 240 |
| AACGTGATCG AGCAGCCCGG CAGCTCCCTG GCCAGCAACA GGATCCTGAC CCTGCCCCAG | 300 |

TABLE 13-continued

| T-HyPB (SEQ ID NO: 17) | |
|---|---|
| AGGACCATCA GGGGCAAGAA CAAGCACTGC TGGTCCACCT CCAAGCCCAC CAGGCGGAGC | 360 |
| AGGGTGTCCG CCCTGAACAT CGTGAGAAGC CAGAGGGGCC CCACCAGGAT GTGCAGGAAC | 420 |
| ATCTACGACC CCCTGCTGTG CTTCAAGCTG TTCTTCACCG ACGAGATCAT CAGCGAGATC | 480 |
| GTGAAGTGGA CCAACGCCGA GATCAGCCTG AAGAGGCGGG AGAGCATGAC CTCCGCCACC | 540 |
| TTCAGGGACA CCAACGAGGA CGAGATCTAC GCCTTCTTCG GCATCCTGGT GATGACCGCC | 600 |
| GTGAGGAAGG ACAACCACAT GAGCACCGAC GACCTGTTCG ACAGATCCCT GAGCATGGTG | 660 |
| TACGTGAGCG TGATGAGCAG GGACAGATTC GACTTCCTGA TCAGATGCCT GAGGATGGAC | 720 |
| GACAAGAGCA TCAGGCCCAC CCTGCGGGAG AACGACGTGT TCACCCCCGT GAGAAAGATC | 780 |
| TGGGACCTGT TCATCCACCA GTGCATCCAG AACTACACCC CTGGCGCCCA CCTGACCATC | 840 |
| GACGAGCAGC TGCTGGGCTT CAGGGGCAGG TGCCCCTTCA GGGTCTATAT CCCCAACAAG | 900 |
| CCCAGCAAGT ACGGCATCAA GATCCTGATG ATGTGCGACA GCGGCACCAA GTACATGATC | 960 |
| AACGGCATGC CCTACCTGGG CAGGGGCACC CAGACCAACG GCGTGCCCCT GGGCGAGTAC | 1020 |
| TACGTGAAGG AGCTGTCCAA GCCCGTCCAC GGCAGCTGCA GAAACATCAC CTGCGACAAC | 1080 |
| TGGTTCACCA GCATCCCCCT GGCCAAGAAC CTGCTGCAGG AGCCCTACAA GCTGACCATC | 1140 |
| GTGGGCACCG TGAGAAGCAA CAAGAGAGAG ATCCCCGAGG TCCTGAAGAA CAGCAGGTCC | 1200 |
| AGGCCCGTGG GCACCAGCAT GTTCTGCTTC GACGGCCCCC TGACCCTGGT GTCCTACAAG | 1260 |
| CCCAAGCCCG CCAAGATGGT GTACCTGCTG TCCAGCTGCG ACGAGGACGC CAGCATCAAC | 1320 |
| GAGAGCACCG GCAAGCCCCA GATGGTGATG TACTACAACC AGACCAAGGG CGGCGTGGAC | 1380 |
| ACCCTGGACC AGATGTGCAG CGTGATGACC TGCAGCAGAA AGACCAACAG GTGGCCCATG | 1440 |
| GCCCTGCTGT ACGGCATGAT CAACATCGCC TGCATCAACA GCTTCATCAT CTACAGCCAC | 1500 |
| AACGTGAGCA GCAAGGGCGA GAAGGTGCAG AGCCGGAAAA AGTTCATGCG GAACCTGTAC | 1560 |
| ATGGGCCTGA CCTCCAGCTT CATGAGGAAG AGGCTGGAGG CCCCCACCCT GAAGAGATAC | 1620 |
| CTGAGGGACA ACATCAGCAA CATCCTGCCC AAAGAGGTGC CCGGCACCAG CGACGACAGC | 1680 |
| ACCGAGGAGC CCGTGATGAA GAAGAGGACC TACTGCACCT ACTGTCCCAG CAAGATCAGA | 1740 |
| AGAAAGGCCA GCGCCAGCTG CAAGAAGTGT AAGAAGGTCA TCTGCCGGGA GCACAACATC | 1800 |
| GACATGTGCC AGAGCTGTTT CTGA | 1824 |

TABLE 14

| TS-HyPB (SEQ ID NO: 18) | |
|---|---|
| ATGGGCGGCA GAAAGAAGAG AAGACAGAGA AGAAGACCCC CCGCCGGCAC CAGCGTGAGC | 60 |
| CTGAAGAAGA AGAGAAAGGT GCCCCCCGCC TCCTCCCTCG ATGACGAGCA CATTCTGTCC | 120 |
| GCTCTGCTGC AGTCCGACGA TGAGCTGGTC GGAGAAGACA GCGATAGCGA GGTGAGCGAC | 180 |
| CACGTCTCCG AGGACGACGT CCAAAGCGAC ACAGAGGAGG CCTTCATCGA CGAGGTGCAC | 240 |
| GAGGTGCAGC CTACCAGCAG CGGCTCCGAG ATCCTGGACG AGCAGAACGT GATCGAGCAG | 300 |
| CCCGGCAGCT CCCTGGCCAG CAACAGGATC CTGACCCTGC CCCAGAGGAC CATCAGGGGC | 360 |
| AAGAACAAGC ACTGCTGGTC CACCTCCAAG CCCACCAGGC GGAGCAGGGT GTCCGCCCTG | 420 |
| AACATCGTGA GAAGCCAGAG GGGCCCCACC AGGATGTGCA GGAACATCTA CGACCCCCTG | 480 |
| CTGTGCTTCA AGCTGTTCTT CACCGACGAG ATCATCAGCG AGATCGTGAA GTGGACCAAC | 540 |
| GCCGAGATCA GCCTGAAGAG GCGGGAGAGC ATGACCTCCG CCACCTTCAG GGACACCAAC | 600 |

TABLE 14-continued

| TS-HyPB (SEQ ID NO: 18) | |
|---|---|
| GAGGACGAGA TCTACGCCTT CTTCGGCATC CTGGTGATGA CCGCCGTGAG GAAGGACAAC | 660 |
| CACATGAGCA CCGACGACCT GTTCGACAGA TCCCTGAGCA TGGTGTACGT GAGCGTGATG | 720 |
| AGCAGGGACA GATTCGACTT CCTGATCAGA TGCCTGAGGA TGGACGACAA GAGCATCAGG | 780 |
| CCCACCCTGC GGGAGAACGA CGTGTTCACC CCCGTGAGAA AGATCTGGGA CCTGTTCATC | 840 |
| CACCAGTGCA TCCAGAACTA CACCCCTGGC GCCCACCTGA CCATCGACGA GCAGCTGCTG | 900 |
| GGCTTCAGGG GCAGGTGCCC CTTCAGGGTC TATATCCCCA ACAAGCCCAG CAAGTACGGC | 960 |
| ATCAAGATCC TGATGATGTG CGACAGCGGC ACCAAGTACA TGATCAACGG CATGCCCTAC | 1020 |
| CTGGGCAGGG GCACCCAGAC CAACGGCGTG CCCCTGGGCG AGTACTACGT GAAGGAGCTG | 1080 |
| TCCAAGCCCG TCCACGGCAG CTGCAGAAAC ATCACCTGCG ACAACTGGTT CACCAGCATC | 1140 |
| CCCCTGGCCA AGAACCTGCT GCAGGAGCCC TACAAGCTGA CCATCGTGGG CACCGTGAGA | 1200 |
| AGCAACAAGA GAGAGATCCC CGAGGTCCTG AAGAACAGCA GGTCCAGGCC CGTGGGCACC | 1260 |
| AGCATGTTCT GCTTCGACGG CCCCCTGACC CTGGTGTCCT ACAAGCCCAA GCCCGCCAAG | 1320 |
| ATGGTGTACC TGCTGTCCAG CTGCGACGAG GACGCCAGCA TCAACGAGAG CACCGGCAAG | 1380 |
| CCCCAGATGG TGATGTACTA CAACCAGACC AAGGGCGGCG TGGACACCCT GGACCAGATG | 1440 |
| TGCAGCGTGA TGACCTGCAG CAGAAAGACC AACAGGTGGC CCATGGCCCT GCTGTACGGC | 1500 |
| ATGATCAACA TCGCCTGCAT CAACAGCTTC ATCATCTACA GCCACAACGT GAGCAGCAAG | 1560 |
| GGCGAGAAGG TGCAGAGCCG GAAAAAGTTC ATGCGGAACC TGTACATGGG CCTGACCTCC | 1620 |
| AGCTTCATGA GGAAGAGGCT GGAGGCCCCC ACCCTGAAGA GATACCTGAG GGACAACATC | 1680 |
| AGCAACATCC TGCCCAAAGA GGTGCCCGGC ACCAGCGACG ACAGCACCGA GGAGCCCGTG | 1740 |
| ATGAAGAAGA GGACCTACTG CACCTACTGT CCCAGCAAGA TCAGAAGAAA GGCCAGCGCC | 1800 |
| AGCTGCAAGA AGTGTAAGAA GGTCATCTGC CGGGAGCACA ACATCGACAT GTGCCAGAGC | 1860 |
| TGTTTCTGA | 1869 |

These DNA sequences of modified piggyBac transposase were produced by chemically synthesizing the N-terminal DNA sequence of TAT NLS or TAT-SV40 NLS and HyPB, and then linking the resulting synthetic DNA sequence to the DNA sequence of HyPB from which the synthetic N-terminal sequence had been removed.

Synthesis of DNA Sequence of Modified PiggyBac Transposase of Second Embodiment A DNA sequence shown in Table 15 (SEQ ID NO: 19), in which TAT-SV40 NLS (SEQ ID NO: 10) and LT-J/Rb (SEQ ID NO: 16) were linked, was added to an N-terminus of HyPB via a linker sequence, whereby TS-LTJ/Rb-HyPB (SEQ ID NO: 20) shown in Table 16 was produced.

TABLE 15

| TAT-SV40LT-NLS-added T-J/Rb (SEQ ID NO: 19) | |
|---|---|
| ATGGGCGGCA GAAAGAAGAG AAGACAGAGA AGAAGACCCC CCGCCGGCAC CAGCGTGAGC | 60 |
| CTGAAGAAGA AGAGAAAGGT GCCCCCCGCC GATAAAGTTT TAAACAGAGA GGAATCTTTG | 120 |
| CAGCTAATGG ACCTTCTAGG TCTTGAAAGG AGTGCCTGGG GGAATATTCC TCTGATGAGA | 180 |
| AAGGCATATT TAAAAAAATG CAAGGAGTTT CATCCTGATA AAGGAGGAGA TGAAGAAAAA | 240 |
| ATGAAGAAAA TGAATACTCT GTACAAGAAA ATGGAAGATG GAGTAAAATA TGCTCATCAA | 300 |

TABLE 15-continued

| TAT-SV40LT-NLS-added T-J/Rb (SEQ ID NO: 19) | |
|---|---|
| CCTGACTTTG GAGGCTTCTG GGATGCAACT GAGATTCCAA CCTATGGAAC TGATGAATGG | 360 |
| GAGCAGTGGT GGAATGCCTT TAATGAGGAA AACCTGTTTT GCTCAGAAGA AATGCCATCT | 420 |
| AGTGATGATG AGGCTACTGC TGACTCTCAA CATTCTACTC CTCCAAAAAA GAAGAGAAAG | 480 |
| GTAGAA | 486 |

TABLE 16

| TS-LTJ-HyPB (SEQ ID NO: 20) | |
|---|---|
| ATGGGCGGCA GAAAGAAGAG AAGACAGAGA AGAAGACCCC CCGCCGGCAC CAGCGTGAGC | 60 |
| CTGAAGAAGA AGAGAAAGGT GCCCCCCGCC GATAAAGTTT TAAACAGAGA GGAATCTTTG | 120 |
| CAGCTAATGG ACCTTCTAGG TCTTGAAAGG AGTGCCTGGG GGAATATTCC TCTGATGAGA | 180 |
| AAGGCATATT TAAAAAAATG CAAGGAGTTT CATCCTGATA AAGGAGGAGA TGAAGAAAAA | 240 |
| ATGAAGAAAA TGAATACTCT GTACAAGAAA ATGGAAGATG GAGTAAAATA TGCTCATCAA | 300 |
| CCTGACTTTG GAGGCTTCTG GGATGCAACT GAGATTCCAA CCTATGGAAC TGATGAATGG | 360 |
| GAGCAGTGGT GGAATGCCTT TAATGAGGAA AACCTGTTTT GCTCAGAAGA AATGCCATCT | 420 |
| AGTGATGATG AGGCTACTGC TGACTCTCAA CATTCTACTC CTCCAAAAAA GAAGAGAAAG | 480 |
| GTAGAAGGTG GTGGTGGTTC TGGTGGTGGT GGTTCTTCCT CCCTCGATGA CGAGCACATT | 540 |
| CTGTCCGCTC TGCTGCAGTC CGACGATGAG CTGGTCGGAG AAGACAGCGA TAGCGAGGTG | 600 |
| AGCGACCACG TCTCCGAGGA CGACGTCCAA AGCGACACAG AGGAGGCCTT TATCATCGAC | 660 |
| GAGGTGCACG AGGTGCAGCC TACCAGCAGC GGCTCCGAGA TCCTGGACGA GCAGAACGTG | 720 |
| ATCGAGCAGC CCGGCAGCTC CCTGGCCAGC AACAGGATCC TGACCCTGCC CCAGAGGACC | 780 |
| ATCAGGGGCA AGAACAAGCA CTGCTGGTCC ACCTCCAAGC CCACCAGGCG GAGCAGGGTG | 840 |
| TCCGCCCTGA ACATCGTGAG AAGCCAGAGG GGCCCCACCA GGATGTGCAG GAACATCTAC | 900 |
| GACCCCCTGC TGTGCTTCAA GCTGTTCTTC ACCGACGAGA TCATCAGCGA GATCGTGAAG | 960 |
| TGGACCAACG CCGAGATCAG CCTGAAGAGG CGGGAGAGCA TGACCTCCGC CACCTTCAGG | 1020 |
| GACACCAACG AGGACGAGAT CTACGCCTTC TTCGGCATCC TGGTGATGAC CGCCGTGAGG | 1080 |
| AAGGACAACC ACATGAGCAC CGACGACCTG TTCGACAGAT CCCTGAGCAT GGTGTACGTG | 1140 |
| AGCGTGATGA GCAGGGACAG ATTCGACTTC CTGATCAGAT GCCTGAGGAT GGACGACAAG | 1200 |
| AGCATCAGGC CCACCCTGCG GGAGAACGAC GTGTTCACCC CCGTGAGAAA GATCTGGGAC | 1260 |
| CTGTTCATCC ACCAGTGCAT CCAGAACTAC ACCCCTGGCG CCCACCTGAC CATCGACGAG | 1320 |
| CAGCTGCTGG GCTTCAGGGG CAGGTGCCCC TTCAGGGTCT ATATCCCCAA CAAGCCCAGC | 1380 |
| AAGTACGGCA TCAAGATCCT GATGATGTGC GACAGCGGCA CCAAGTACAT GATCAACGGC | 1440 |
| ATGCCCTACC TGGGCAGGGG CACCCAGACC AACGGCGTGC CCCTGGGCGA GTACTACGTG | 1500 |
| AAGGAGCTGT CCAAGCCCGT CCACGGCAGC TGCAGAAACA TCACCTGCGA CAACTGGTTC | 1560 |
| ACCAGCATCC CCCTGGCCAA GAACCTGCTG CAGGAGCCCT ACAAGCTGAC CATCGTGGGC | 1620 |
| ACCGTGAGAA GCAACAAGAG AGAGATCCCC GAGGTCCTGA AGAACAGCAG GTCCAGGCCC | 1680 |
| GTGGGCACCA GCATGTTCTG CTTCGACGGC CCCCTGACCC TGGTGTCCTA CAAGCCCAAG | 1740 |
| CCCGCCAAGA TGGTGTACCT GCTGTCCAGC TGCGACGAGG ACGCCAGCAT CAACGAGAGC | 1800 |
| ACCGGCAAGC CCCAGATGGT GATGTACTAC AACCAGACCA AGGGCGGCGT GGACACCCTG | 1860 |

TABLE 16-continued

| TS-LTJ-HyPB (SEQ ID NO: 20) | |
|---|---|
| GACCAGATGT GCAGCGTGAT GACCTGCAGC AGAAAGACCA ACAGGTGGCC CATGGCCCTG | 1920 |
| CTGTACGGCA TGATCAACAT CGCCTGCATC AACAGCTTCA TCATCTACAG CCACAACGTG | 1980 |
| AGCAGCAAGG GCGAGAAGGT GCAGAGCCGG AAAAAGTTCA TGCGGAACCT GTACATGGGC | 2040 |
| CTGACCTCCA GCTTCATGAG GAAGAGGCTG GAGGCCCCCA CCCTGAAGAG ATACCTGAGG | 2100 |
| GACAACATCA GCAACATCCT GCCCAAAGAG GTGCCCGGCA CCAGCGACGA CAGCACCGAG | 2160 |
| GAGCCCGTGA TGAAGAAGAG GACCTACTGC ACCTACTGTC CCAGCAAGAT CAGAAGAAAG | 2220 |
| GCCAGCGCCA GCTGCAAGAA GTGTAAGAAG GTCATCTGCC GGGAGCACAA CATCGACATG | 2280 |
| TGCCAGAGCT GTTTCTGA | 2298 |

TS-LTJ/Rb-HyPB was produced by chemically synthesizing DNA sequences of the N-termini of TAT-SV40 NLS, LTJ/Rb, the linker sequence, and HyPB, and then linking the resulting sequence to the DNA sequence of HyPB from which the synthetic N-terminal sequence was removed. Further, a DNA sequence shown in Table 17 (TS-LTJ/Rb, SEQ ID NO: 21) was produced as a polypeptide of the cell division promoting domain alone that does not link to PB.

TABLE 17

| TS-LTJ/Rb (SEQ ID NO: 21) | |
|---|---|
| ATGGGCGGCA GAAAGAAGAG AAGACAGAGA AGAAGACCCC CCGCCGGCAC CAGCGTGAGC | 60 |
| CTGAAGAAGA AGAGAAAGGT GCCCCCCGCC GATAAAGTTT TAAACAGAGA GGAATCTTTG | 120 |
| CAGCTAATGG ACCTTCTAGG TCTTGAAAGG AGTGCCTGGG GGAATATTCC TCTGATGAGA | 180 |
| AAGGCATATT TAAAAAAATG CAAGGAGTTT CATCCTGATA AAGGAGGAGA TGAAGAAAAA | 240 |
| ATGAAGAAAA TGAATACTCT GTACAAGAAA ATGGAAGATG GAGTAAAATA TGCTCATCAA | 300 |
| CCTGACTTTG GAGGCTTCTG GGATGCAACT GAGATTCCAA CCTATGGAAC TGATGAATGG | 360 |
| GAGCAGTGGT GGAATGCCTT TAATGAGGAA AACCTGTTTT GCTCAGAAGA AATGCCATCT | 420 |
| AGTGATGATG AGGCTACTGC TGACTCTCAA CATTCTACTC CTCCAAAAAA GAAGAGAAAG | 480 |
| GTAGAATGA | 489 |

TS-LTJ/Rb was produced through chemical synthesis by adding a stop codon to the terminus of the DNA sequence of TAT-SV40 NLS and LT-J/Rb.

Example 2 Production of Plasmid

As template DNA for RNA preparation of modified PB, a plasmid was produced in which the DNA sequences of PB (WtPB, HuPB, HyPB, T-HyPB, TS-HyPB, and TS-LTJ/Rb-HyPB) obtained in Example 1 were incorporated into pGEM-GL-pA.

pGEM-GL-pA was produced by inserting the leader sequence of human β-globin (Globin leader) and the poly (A) sequence of pSP64 pA vector (Promega Corporation) into the commercially available plasmid DNA for RNA synthesis containing the T7 promoter and the poly (A) sequence: pGEM (registered trademark)-4Z (Promega Corporation). The DNA sequence of PB obtained in Example 1 was incorporated between the human β-globin leader sequence and the poly (A) sequence of pGEM-GL-pA.

Further, there was produced template DNA for RNA preparation of the cell division promoting domain (TS-LTJ/Rb) unlinked to the PB domain. This template DNA plasmid was produced by incorporating the TS-LTJ/Rb DNA sequence between the human β-globin leader sequence and the poly (A) sequence of pGEM-GL-pA.

Example 3 Synthesis of mRNA

The pGEM-GL-pA obtained in Example 2 was used to synthesize mRNA as described below. First, the plasmid DNA was cut with the restriction enzyme EcoRI and purified, and then 20 μL of an in vitro transcription reaction solution containing 1.0 μg of template DNA was prepared and reacted in a constant temperature bath at 37° C. for 2 hours. To the in vitro transcription reaction solution, three types of nucleotides (ATP, CTP, and GTP) supplied in the CUGA (registered trademark) 7 kit and the nucleotide analog ψUTP (Jena Bioscience GmbH) were added. The RNA synthesis procedure was conducted according to the protocol of the CUGA (registered trademark) 7 kit.

After completion of the reaction, synthetic RNA was purified with MEGAclear™ transcription Clean-Up kit (Invitrogen Corporation). The purification of RNA was conducted according to the procedure for the kit.

After purification, a Cap structure and a poly (A) structure were added to the 5'-UTR and 3'-UTR of RNA, respectively, to form mRNA. The Cap structure and the poly (A) structure were added using the ScriptCap™ m7G Capping System (CellScript) and the ScriptCap™ 2'-O-Metyltransferase Kit (CellScript). The operation was performed as follows according to the manual of the kit.

The resulting RNA was incubated at 65° C. for 10 minutes and then immediately placed on ice to disrupt the secondary structure of the RNA. 100 μL of a Capping reaction solution containing 60 μg of this RNA was prepared and reacted in a constant temperature bath at 37° C. for 1 hour in order to add the Cap structure to the 5'-UTR of RNA. The A-Plus™ Poly (A) Polymerase Tailing kit (CellScript) was added to the same solution, and the mixture was reacted in a constant temperature bath at 37° C. for 2 hours in order to add the poly (A) structure to the 3'-UTR. After completion of the reaction, the mRNA in the reaction solution was purified by the ammonium acetate precipitation method according to the manual of the kit. The absorbance (A260) was measured using a spectrophotometer (BioSpec-mini, Shimadzu Corporation) and the RNA concentration was calculated as OD1.0=40.0 μg/mL RNA.

Example 4 Preparation of mRNA-Encapsulating Liposomes

1/20 amount of mRNA solution (1.6 μg/mL) was added to 100 μL of ethanol lipid solution (FFT20 (the compound of Formula (1-02) above)/DOTAP/DOPE/cholesterol/PEG-DMG=37/10.5/5.25/60/4 (mole ratio)) to prepare 105 μL of RNA-containing lipid solution, and then 695 μL of 10 mM HEPES (pH 7.3) was gently added to form a liposome solution. Four sets of this liposome solution were prepared, and these solutions were concentrated by centrifugation at 14,000×g using a centrifugal ultrafiltration tube: Amicon Ultra 0.5 mL, Ultracel-50K (Millipore Corporation). After the concentration, buffer exchange and concentration were carried out by adding 400 μL of 10 mM HEPES (pH 7.3) and the final volume was adjusted to 100 μL. The amount of RNA contained in the liposome was measured by the QuantiFluor™ RNA System (Promega Corporation).

Example 5 Measurement of Transposon Excision Activities of WtPB, HuPB, and HyPB

The transposon (TP) excision activity of each of the above-described modified piggyBac transposases was measured using plasmid DNA for measuring TP excision activity: pMSCV-SpNL.

NanoLuc (registered trademark) gene (Promega Corporation) (Oplophorus gracilirostris derived-luciferase) whose cording sequence split into two; the N-terminal part and the C-terminal part is incorporated into pMSCV-SpNL, and TP having piggyBac transposase recognition sequences (transposon terminal sequences, 5'-IR and 3'-IR) is inserted between the split NanoLuc (registered trademark) genes. A mouse stem cell virus (MSCV) promoter was linked to the upstream of the N-terminal side (NLuc-N) of the split NanoLuc (registered trademark) RNA gene (Split-NLuc), and a poly (A) addition signal sequence of bovine growth hormone (BGH) gene was linked to the downstream of the C-terminal side (NLuc-C).

In pMSCV-SpNL, the NanoLuc (registered trademark) gene as a luciferase was split into two parts; the N-terminal part and the C-terminal part, by inserting TP. In this state, the active NanoLuc (registered trademark) is not expressed in cells. However, after being introduced to the cells, TP is excised by transposase, the N-terminus and C-terminus of NanoLuc (registered trademark) are linked by the DNA repair mechanism of the cells, whereby the active NanoLuc (registered trademark) gene is formed. As a result, the active NanoLuc (registered trademark) is expressed in the cells and the cells emit light.

Therefore, the luminescence intensity of cells is correlated with the TP excision activity of the transposases. Consequently, pMSCV-SpNL can be used to quantify the TP excision activity of PB as the luminescence intensity of cells.

Human acute leukemia cells: Jurkat (ATCC) were used as cells. Jurkat cells cultured in TexMACS (Miltenyi Biotec) were suspended in a culture medium at a density of 5.0×106 cells/mL, and 50 μL of the resulting suspension was added to the wells of a 96-well culture plate.

50 μL of TexMACS was added to the wells and mixed gently. Thereafter, the WtPB-mRNA-encapsulating liposomes, HuPB-mRNA-encapsulating liposomes or HyPB-mRNA-encapsulating liposomes (0.5 μg/well) produced in Example 4 and pMSCV-SpNL (0.5 μg/well) were added, and the cells were cultured in an incubator at 37° C. in a 5% CO2 atmosphere. After 72 hours, the culture plate was removed from the incubator, the cells were pipetted and suspended, and then 50 μL of the cell suspension was transferred to a 96-well black plate (Thermo Fisher Scientific). To the plate, the NanoLuc (registered trademark) assay solution (Nano-Glo (registered trademark) Luciferase Assay System, Promega Corporation) was added in an equal amount. After mixing at room temperature for 5 minutes, the luminescence intensity of the wells of the black plate was measured with a luminometer (Infinite (registered trademark) F200PRP, Tecan Group Ltd.).

Figure 7:
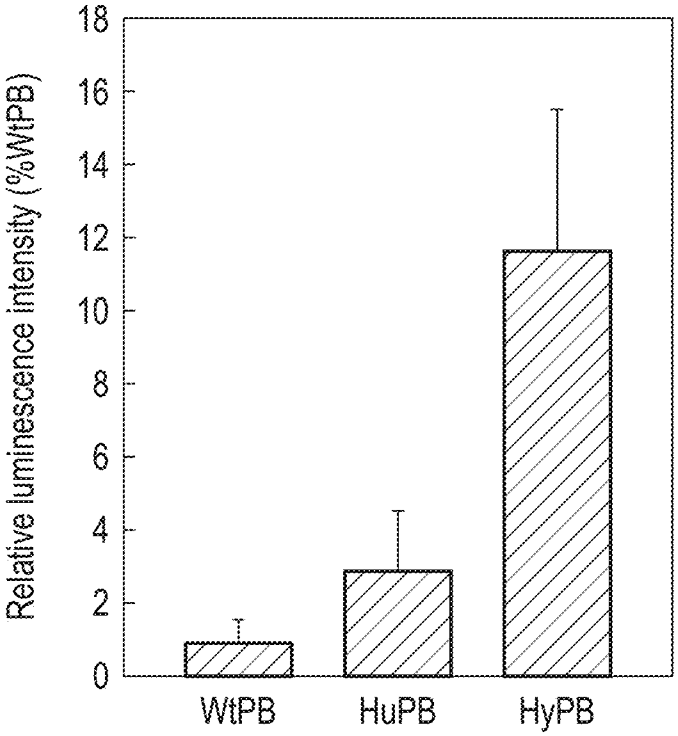
FIG. 7 is a graph showing experimental results in Example 5.

The results were shown in FIG. 7. The TP excision activity of HuPB was about 3 times that of WtPB and the TP excision activity of HyPB was about 11 times that of WtPB. Therefore, it was shown that HuPB and HyPB had excellent TP excision activity.

Example 6 Measurement of TP Excision Activities of T-HyPB and TS-HyPB

T-HyPB-mRNA-encapsulating liposomes and TS-HyPB-mRNA-encapsulating liposomes were used, and the TP excision activity was measured by the method described in Example 5.

Figure 8:
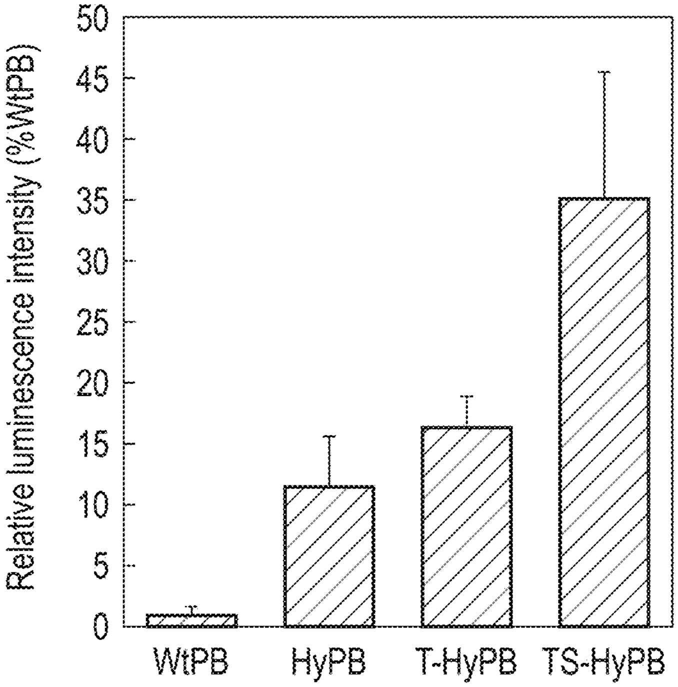
FIG. 8 is a graph showing experimental results in Example 6.

The results were shown in FIG. 8. The TP excision activity of T-HyPB was about 1.4 times the activity of HyPB alone, and the TP excision activity of TS-HyPB was about 3 times the activity of HyPB alone. Further, the TP excision activity of T-HyPB is about 16 times the activity of WtPB and the TP excision activity of TS-HyPB is about 36 times the activity of WtPB. This indicated that both T-HyPB and TS-HyPB had excellent TP excision activity.

Example 7 Measurement of TP Excision Activity of TS-LTJ/Rb-HyPB

The TP excision activity was measured by the method described in Example 5 using TS-LTJ/Rb-HyPB-mRNA-encapsulating liposomes.

Figure 9:
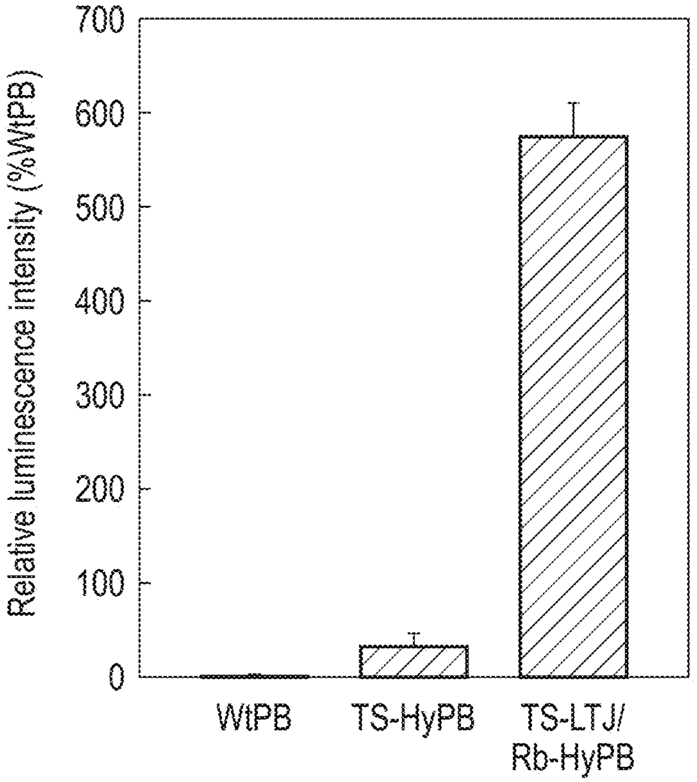
FIG. 9 is a graph showing experimental results in Example 7.

The results were shown in FIG. 9. The TP excision activity of TS-LTJ/Rb-HyPB to which a cell division promoting peptide was added was increased about 16 times that of TS-HyPB and about 570 times that of WtPB. Therefore, it was shown that further excellent TP excision activity was obtained by further adding the cell division promoting domain.

Example 8 Production of CAR-T using WtPB, TS-HyPB, and TS-LTJ/Rb-HyPB

Chimeric antibody-incorporated T cells (CAR-T) were produced by the transposon method as described below using the WtPB-mRNA-encapsulating liposomes, TS-HyPB-mRNA-encapsulating liposomes, and TS-LTJ/Rb-HyPB-mRNA-encapsulating liposome produced in Example 4.

As the donor DNA, plasmid DNA containing CAR transposon (pIRII-CAR.CD19 (CD28)) was used. Preparation of plasmid DNA-encapsulating liposomes was conducted according to the liposome preparation method described in Example 4. As cells, human peripheral blood mononuclear cells (PBMCs) were used.

PBMCs cultured overnight were collected by centrifugation at 200×g for 10 minutes, and then suspended in TexMACS supplemented with cytokines (IL-7, 10 ng/mL; IL-15, 5 ng/mL) to prepare a 2.0×106 cells/mL cell suspension. 500 μL of the cell suspension was seeded on a 48-well culture plate coated with CD3/CD28 antibody and cultured at 37° C. in a 5% CO2 atmosphere. The culture plate was coated by adding 150 μL of CD3/CD28 antibody solution diluted 100-fold with phosphate buffered saline (PBS) to each well of the 48-well culture plate (Non-tissue culture treated, Nunc), and allowing the solution to stand at 37° C. in a 5% CO2 atmosphere for 2 hours or more.

24 hours after seeding of PBMCs, plasmid DNA-encapsulating liposomes (4.0 μg/well) and PB-mRNA-encapsulating liposomes (4.0 μg/well) were added, and the cells were cultured at 37° C. in a 5% CO2 atmosphere.

Two weeks later, the PBMCs were removed from the incubator and the CAR-T production rate was examined with a fluorescence activated cell sorter (FACS) as described below. BD Biosciences FACS Verse was used for FACS. The PBMCs were collected and then washed once with PBS, and the cells were suspended in 50 μL of PBS. To the suspension, 2 μL of anti-human IgG (H+L) antibody [FITC F(ab')2 Fragment Goat Anti-Human IgG(H+L)antibody, The Jackson Laboratory] was added, and an antigen-antibody reaction was carried out at 4° C. for 15 minutes. After completion of the reaction, the cells were washed once with PBS, the cells were suspended in 50 μL of PBS, and 2 μL of anti-CD3 antibody (V450 Mouse Anti-Human CD3, Clone UCHT1, BD Biosciences) was added. After the antigen-antibody reaction at 4° C. for 15 minutes, the cells were washed once with PBS and then suspended in 1% BSA/PBS to prepare a sample for FACS analysis. In the FACS, green fluorescence (FITC) of CAR-expressing cells and blue fluorescence (V450) of CD3-expressing T cells were detected. CAR-T cells are cells in which green fluorescence and blue fluorescence are co-positive (CAR-positive and CD3-positive cells). The CAR-T production rate was a ratio of CAR-T cells to all detected cells.

Figure 10:
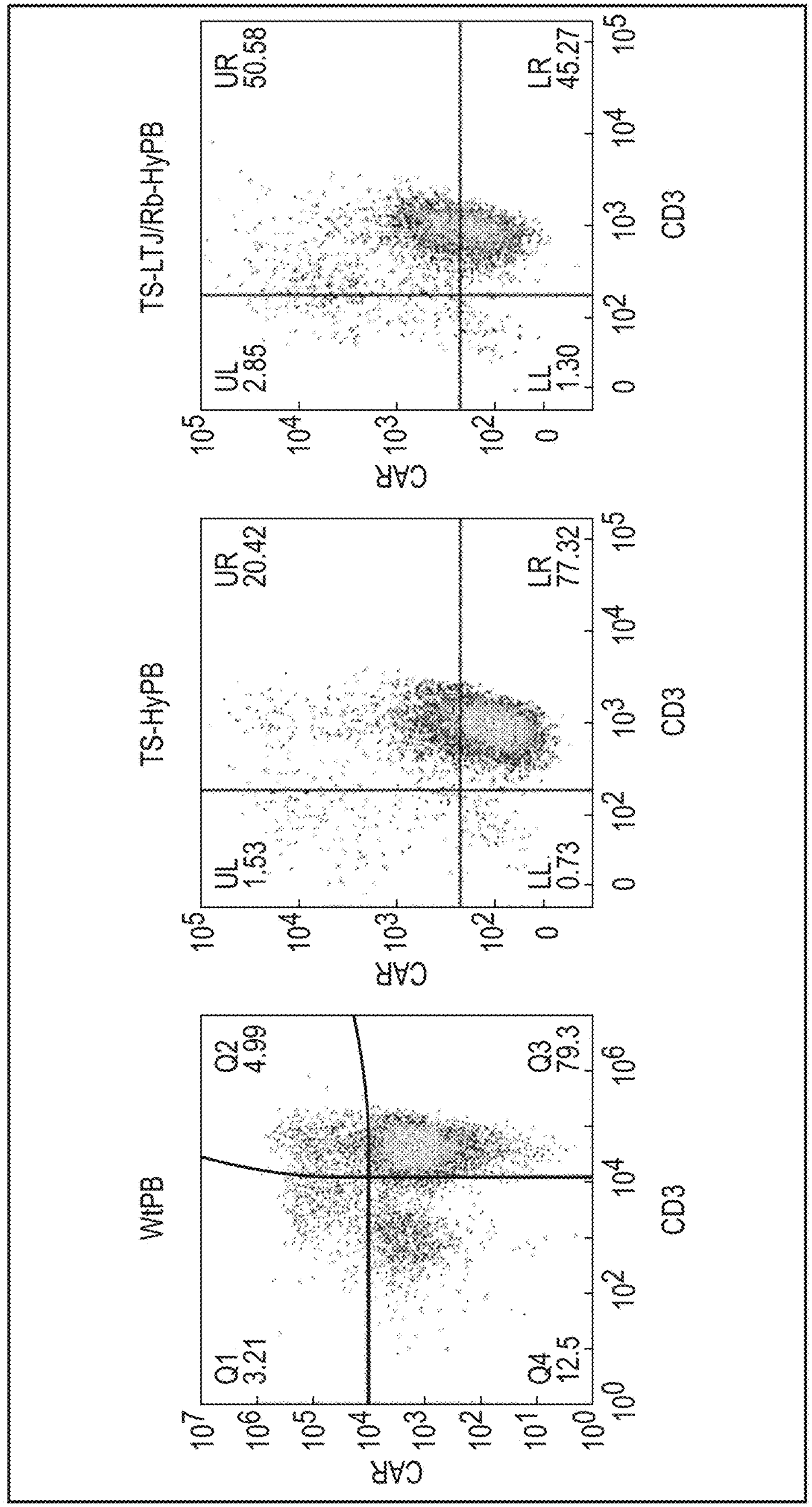
FIG. 10 is a graph showing experimental results in Example 8.

The results were shown in FIG. 10. In WtPB, CAR-T cells are cells in the Q2 region. In TS-HyPB and TS-LTJ/Rb-HyPB, CAR-T cells are cells in the UR region (CAR/CD3 co-positive region). The CAR-T production rate in WtPB was about 5%, as illustrated in the graph of FIG. 10. In contrast, the CAR-T production rate in TS-HyPB was about 20%, which was about 4 times that in WtPB. In addition, the CAR-T production rate in TS-LTJ/Rb-HyPB was about 50%, which was about 10 times that in WtPB.

Therefore, according to the modified piggyBac transposase of the embodiment, it was shown that the cell production efficiency was greatly improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A polynucleotide encoding a modified piggyBac transposase, the polynucleotide comprising:

a) a base sequence encoding a piggyBac transposase comprising an amino acid sequence at least 90% identical to SEQ ID NO: 1;

wherein the encoded amino acid sequence comprises:

a V at the position corresponding to amino acid 30 of SEQ ID NO: 1, a P at the position corresponding to amino acid 103 of SEQ ID NO: 1, an S at the position corresponding to amino acid 165 of SEQ ID NO: 1, a V at the position corresponding to amino acid 282 of SEQ ID NO: 1, a G at the position corresponding to amino acid 509 of SEQ ID NO: 1, a K at the position corresponding to amino acid 538 of SEQ ID NO: 1, and an S at the position corresponding to amino acid 571 of SEQ ID NO: 1;

and b) a base sequence encoding a nuclear localization signal functionally linked to the encoded piggyBac transposase;

wherein the polynucleotide comprises the base sequence of SEQ ID NO: 17 or SEQ ID NO: 18, or the polynucleotide comprises the RNA equivalent of the base sequence of SEQ ID NO: 17 or SEQ ID NO: 18.

2. The polynucleotide of claim 1, wherein the polynucleotide is DNA or RNA.

3. The polynucleotide of claim 1 wherein at least one codon among codons corresponding to amino acids constituting the modified piggyBac transposase is selected from the following codons for each of the amino acids:

GCU or GCC for alanine (A);
UGC or UGU for cysteine (C);
GAC or GAU for aspartic acid (D);
GAA or GAG for glutamic acid (E);
UUC or UUU for phenylalanine (F);
GGA or GGC for glycine (G);
CAC or CAU for histidine (H);
AUC or AUU for isoleucine (I);
AAA or AAG for lysine (K);
CUC or CUG for leucine (L);

AUG for methionine (M);
AAC or AAU for asparagine (N);
CCC or CCU for proline (P);
CAA or CAG for glutamine (Q);
AGA or AGG for arginine (R);
AGC, UCC or UCU for serine(S);
ACA or ACC for threonine (T);
GUC or GUG for valine (V);
UGG for tryptophan (W);
UAC or UAU for tyrosine (Y); and
UGA for a stop codon,
wherein A is adenine, U is uracil, C is cytosine, G is guanine, and when the polynucleotide is DNA, U is changed to thymine (T).

4. The polynucleotide of claim 1, wherein the polynucleotide is DNA and the base sequence encoding the nuclear localization signal comprises the sequence of SEQ ID NO: 8, 9 or 10.

5. A polynucleotide encoding a modified piggyBac transposase, the polynucleotide comprising:
a) a base sequence encoding a piggyBac transposase comprising an amino acid sequence at least 90% identical to SEQ ID NO: 1;
wherein the encoded amino acid sequence comprises:
a V at the position corresponding to amino acid 30 of SEQ ID NO: 1,
a P at the position corresponding to amino acid 103 of SEQ ID NO: 1,
an S at the position corresponding to amino acid 165 of SEQ ID NO: 1,
a V at the position corresponding to amino acid 282 of SEQ ID NO: 1,
a G at the position corresponding to amino acid 509 of SEQ ID NO: 1,
a K at the position corresponding to amino acid 538 of SEQ ID NO: 1, and
an S at the position corresponding to amino acid 571 of SEQ ID NO: 1;
b) a base sequence encoding a nuclear localization signal functionally linked to the encoded piggyBac transposase; and
c) a base sequence encoding a peptide that promotes cell division.

6. A polynucleotide encoding a modified piggyBac transposase, the polynucleotide comprising:
a) a base sequence encoding a piggyBac transposase comprising an amino acid sequence at least 90% identical to SEQ ID NO: 1;
wherein the encoded amino acid sequence comprises:
a V at the position corresponding to amino acid 30 of SEQ ID NO: 1,
a P at the position corresponding to amino acid 103 of SEQ ID NO: 1,
an S at the position corresponding to amino acid 165 of SEQ ID NO: 1,
a V at the position corresponding to amino acid 282 of SEQ ID NO: 1,
a G at the position corresponding to amino acid 509 of SEQ ID NO: 1,
a K at the position corresponding to amino acid 538 of SEQ ID NO: 1, and
an S at the position corresponding to amino acid 571 of SEQ ID NO: 1;
b) a base sequence encoding a nuclear localization signal functionally linked to the encoded piggyBac transposase; and
c) a base sequence encoding a peptide that promotes cell division;
wherein the polynucleotide comprises the base sequence of SEQ ID NO: 20.

7. An introducing carrier for incorporating a target sequence into a cell genome comprising:
a lipid particle; and
the polynucleotide encoding a modified piggyBac transposase according to claim 1;
wherein the polynucleotide is encapsulated in the lipid particle.

8. The introducing carrier of claim 1,
wherein the polynucleotide further comprises a base sequence encoding a peptide that promotes cell division.

9. The introducing carrier of claim 8, wherein donor DNA containing the target sequence is further encapsulated in the lipid particles.

10. The introducing carrier of claim 7, wherein the lipid particles contain, as a constituent component, a lipid compound represented by Formula (1-01) and/or a lipid compound represented by Formula (1-02).

(1-01)

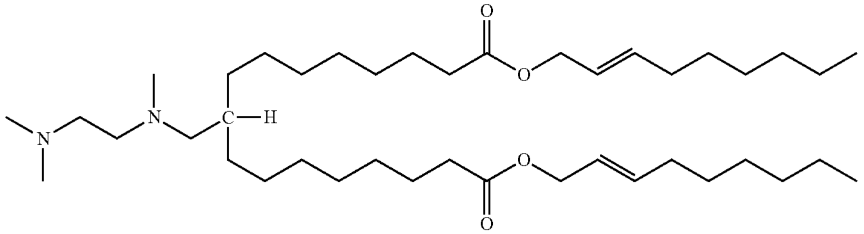

(1-02)

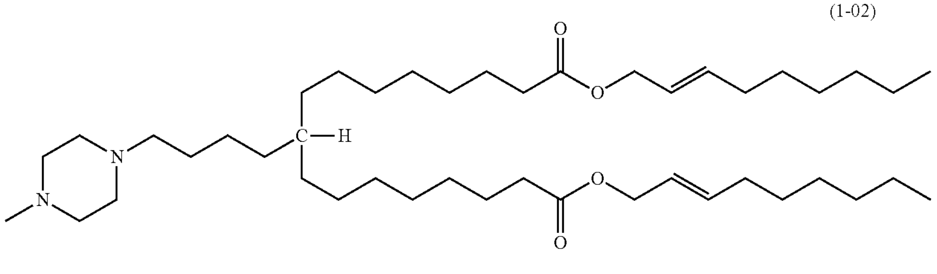

11. A kit for incorporating a target sequence into a cell genome, the kit comprising:

the polynucleotide encoding a modified piggyBac transposase of claim 1; and a donor DNA containing a target sequence.

12. The kit of claim 11, wherein the polynucleotide and the donor DNA are encapsulated in lipid particle.

13. A method of incorporating a target sequence into a cell genome, comprising introducing a donor DNA containing a target sequence into a cell with a polynucleotide encoding a modified piggyBac transposase according to claim 1.

14. The method of claim 13, wherein the polynucleotide further comprises a base sequence encoding a peptide that promotes cell division.

15. The method of claim 13, wherein the introducing is performed using a liposome method, a lipofection method, an electroporation method, a sonoporation method, or a magnetofection method.

16. The method of claim 15, wherein the introducing is performed by using a liposome method comprising contacting the cell with lipid particles encapsulating the donor DNA, and the polynucleotide.

17. A method of producing a cell, comprising introducing donor DNA containing a target sequence into a cell with a polynucleotide encoding a modified piggyBac transposase according to claim 1.

18. The method of claim 17, wherein the polynucleotide further includes a base sequence encoding a peptide that promotes cell division.

19. The method of claim 17, wherein the introducing is performed using a liposome method, a lipofection method, an electroporation method, a sonoporation method, or a magnetofection method.

20. The method of claim 19, wherein the introducing is performed by a liposome method, and lipid particles encapsulating the donor DNA, and the polynucleotide, are brought into contact with the cell.

* * * * *

SEQUENCE LISTING

```
<160> NUMBER OF SEQ ID NOS: 23

<210> SEQ ID NO 1
<211> LENGTH: 594
<212> TYPE: PRT
<213> ORGANISM: Trichoplushia ni

<400> SEQUENCE: 1

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Asp Val Gln Ser Asp Thr Glu Glu Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110
```

-continued

```
Asn Ile Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Lys Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
        515                 520                 525
```

-continued

Arg Asp Asn Ile Ser Asn Ile Leu Pro Asn Glu Val Pro Gly Thr Ser
530 535 540

Asp Asp Ser Thr Glu Glu Pro Val Met Lys Lys Arg Thr Tyr Cys Thr
545 550 555 560

Tyr Cys Pro Ser Lys Ile Arg Arg Lys Ala Asn Ala Ser Cys Lys Lys
565 570 575

Cys Lys Lys Val Ile Cys Arg Glu His Asn Ile Asp Met Cys Gln Ser
580 585 590

Cys Phe

<210> SEQ ID NO 2
<211> LENGTH: 594
<212> TYPE: PRT
<213> ORGANISM: artificial
<220> FEATURE:
<223> OTHER INFORMATION: PB domain

<400> SEQUENCE: 2

Met Gly Ser Ser Leu Asp Asp Glu His Ile Leu Ser Ala Leu Leu Gln
1 5 10 15

Ser Asp Asp Glu Leu Val Gly Glu Asp Ser Asp Ser Glu Val Ser Asp
20 25 30

His Val Ser Glu Asp Asp Val Gln Ser Asp Thr Glu Glu Ala Phe Ile
35 40 45

Asp Glu Val His Glu Val Gln Pro Thr Ser Ser Gly Ser Glu Ile Leu
50 55 60

Asp Glu Gln Asn Val Ile Glu Gln Pro Gly Ser Ser Leu Ala Ser Asn
65 70 75 80

Arg Ile Leu Thr Leu Pro Gln Arg Thr Ile Arg Gly Lys Asn Lys His
85 90 95

Cys Trp Ser Thr Ser Lys Pro Thr Arg Arg Ser Arg Val Ser Ala Leu
100 105 110

Asn Ile Val Arg Ser Gln Arg Gly Pro Thr Arg Met Cys Arg Asn Ile
115 120 125

Tyr Asp Pro Leu Leu Cys Phe Lys Leu Phe Phe Thr Asp Glu Ile Ile
130 135 140

Ser Glu Ile Val Lys Trp Thr Asn Ala Glu Ile Ser Leu Lys Arg Arg
145 150 155 160

Glu Ser Met Thr Ser Ala Thr Phe Arg Asp Thr Asn Glu Asp Glu Ile
165 170 175

Tyr Ala Phe Phe Gly Ile Leu Val Met Thr Ala Val Arg Lys Asp Asn
180 185 190

His Met Ser Thr Asp Asp Leu Phe Asp Arg Ser Leu Ser Met Val Tyr
195 200 205

Val Ser Val Met Ser Arg Asp Arg Phe Asp Phe Leu Ile Arg Cys Leu
210 215 220

Arg Met Asp Asp Lys Ser Ile Arg Pro Thr Leu Arg Glu Asn Asp Val
225 230 235 240

Phe Thr Pro Val Arg Lys Ile Trp Asp Leu Phe Ile His Gln Cys Ile
245 250 255

Gln Asn Tyr Thr Pro Gly Ala His Leu Thr Ile Asp Glu Gln Leu Leu
260 265 270

Gly Phe Arg Gly Arg Cys Pro Phe Arg Val Tyr Ile Pro Asn Lys Pro
275 280 285

Ser Lys Tyr Gly Ile Lys Ile Leu Met Met Cys Asp Ser Gly Thr Lys

-continued 290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Lys Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Gly Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Lys Glu Val Pro Gly Thr Ser
    530                 535                 540

Asp Asp Ser Thr Glu Glu Pro Val Met Lys Lys Arg Thr Tyr Cys Thr
545                 550                 555                 560

Tyr Cys Pro Ser Lys Ile Arg Arg Lys Ala Ser Ala Ser Cys Lys Lys
                565                 570                 575

Cys Lys Lys Val Ile Cys Arg Glu His Asn Ile Asp Met Cys Gln Ser
            580                 585                 590

Cys Phe

<210> SEQ ID NO 3
<211> LENGTH: 6
<212> TYPE: PRT
<213> ORGANISM: SV40

<400> SEQUENCE: 3

Lys Lys Lys Arg Lys Val
1               5

<210> SEQ ID NO 4
<211> LENGTH: 10
<212> TYPE: PRT
<213> ORGANISM: HIV

<400> SEQUENCE: 4

Gly Arg Lys Lys Arg Arg Gln Arg Arg Arg
1               5                   10

-continued

<210> SEQ ID NO 5
<211> LENGTH: 1785
<212> TYPE: DNA
<213> ORGANISM: Trichoplushia ni

<400> SEQUENCE: 5
atgggtagtt ctttagacga tgagcatatc ctctctgctc ttctgcaaag cgatgacgag 60
cttgttggtg aggattctga cagtgaaata tcagatcacg taagtgaaga tgacgtccag 120
agcgatacag aagaagcgtt tatagatgag gtacatgaag tgcagccaac gtcaagcggt 180
agtgaaatat tagacgaaca aaatgttatt gaacaaccag gttcttcatt ggcttctaac 240
agaatcttga ccttgccaca gaggactatt agaggtaaga ataaacattg ttggtcaact 300
tcaaagtcca cgaggcgtag ccgagtctct gcactgaaca ttgtcagatc tcaaagaggt 360
ccgacgcgta tgtgccgcaa tatatatgac ccacttttat gcttcaaact atttttact 420 gatgagataa tttcggaaat tgtaaaatgg acaaatgctg agatatcatt gaaacgtcgg 480
gaatctatga caggtgctac atttcgtgac acgaatgaag atgaaatcta tgctttcttt 540
ggtattctgg taatgacagc agtgagaaaa gataaccaca tgtccacaga tgacctcttt 600
gatcgatctt tgtcaatggt gtacgtctct gtaatgagtc gtgatcgttt tgatttttg 660 atacgatgtc ttagaatgga tgacaaaagt atacggccca cacttcgaga aaacgatgta 720
tttactcctg ttagaaaaat atgggatctc tttatccatc agtgcataca aaattacact 780
ccaggggctc atttgaccat agatgaacag ttacttggtt ttagaggacg gtgtccgttt 840
aggatgtata tcccaaacaa gccaagtaag tatggaataa aaatcctcat gatgtgtgac 900
agtggtacga agtatatgat aaatggaatg ccttatttgg gaagaggaac acagaccaac 960
ggagtaccac tcggtgaata ctacgtgaag gagttatcaa agcctgtgca cggtagttgt 1020
cgtaatatta cgtgtgacaa ttggttcacc tcaatccctt tggcaaaaaa cttactacaa 1080
gaaccgtata agttaaccat tgtgggaacc gtgcgatcaa acaaacgcga gataccggaa 1140
gtactgaaaa acagtcgctc caggccagtg ggaacatcga tgttttgttt tgacggaccc 1200
cttactctcg tctcatataa accgaagcca gctaagatgg tatacttatt atcatcttgt 1260
gatgaggatg cttctatcaa cgaaagtacc ggtaaaccgc aaatggttat gtattataat 1320
caaactaaag gcggagtgga cacgctagac caaatgtgtt ctgtgatgac ctgcagtagg 1380
aagacgaata ggtggcctat ggcattattg tacggaatga taaacattgc ctgcataaat 1440
tcttttatta tatacagcca taatgtcagt agcaagggag aaaaggttca aagtcgcaaa 1500
aaatttatga gaaaccttta catgagcctg acgtcatcgt ttatgcgtaa gcgtttagaa 1560
gctcctactt tgaagagata tttgcgcgat aatatctcta atattttgcc aaatgaagtg 1620
cctggtacat cagatgacag tactgaagag ccagtaatga aaaaacgtac ttactgtact 1680
tactgcccct ctaaaataag gcgaaaggca aatgcatcgt gcaaaaaatg caaaaaagtt 1740
atttgtcgag agcataatat tgatatgtgc caaagttgtt tctga 1785

<210> SEQ ID NO 6
<211> LENGTH: 1785
<212> TYPE: DNA
<213> ORGANISM: artificial
<220> FEATURE:
<223> OTHER INFORMATION: PB domain

<400> SEQUENCE: 6

-continued

```
atgggctcct ccctcgatga cgagcacatt ctgtccgctc tgctgcagtc cgacgatgag     60
ctggtcggag aagacagcga tagcgagatc agcgaccacg tctccgagga cgacgtccaa    120
agcgacacag aggaggcctt tatcgacgag gtccatgaag tgcagcccac atccagcggc    180
agcgagattc tggacgagca gaacgtgatc gaacagcccg gcagctccct cgccagcaat    240
agaattctga cactgcccca gagaaccatt agaggcaaga acaagcactg ttggagcacc    300
agcaagagca caagaagatc cagagtcagc gccctcaaca ttgtgagaag ccagaggggc    360
cctacaagaa tgtgtagaaa catctatgac cctctgctgt gtttcaagct gttcttcacc    420
gacgagatca tcagcgagat cgtgaagtgg accaacgctg agatctctct gaagaggaga    480
gaaagcatga ccggcgccac ctttagggac accaacgagg acgaaatcta tgcttttttt    540
ggaattctgg tgatgacagc cgtgaggaaa gacaaccaca tgtccacaga tgatctgttt    600
gatagatctc tgtccatggt gtatgtgagc gtcatgtcca gagatagatt cgatttcctc    660
attagatgtc tgaggatgga cgataagtcc atcagaccca cactgagaga gaacgacgtc    720
tttacccccg tgagaaaaat ctgggacctc ttcatccacc agtgcatcca aaattataca    780
cccggcgctc acctcaccat cgacgagcag ctcctcggct tcagaggaag atgccccttt    840
agaatgtaca ttcccaacaa gccctccaag tacggcatca agatcctcat gatgtgtgac    900
agcggcacca agtacatgat caacggcatg ccctatctgg gaagaggcac ccagaccaac    960
ggagtgcccc tcggcgaata ttacgtgaag gaactgagca aacccgtgca cggcagctgc   1020
agaaatatta catgcgataa ctggttcacc agcatccctc tggccaaaaa tctgctgcaa   1080
gagccttaca agctcacaat cgtgggaacc gtgaggagca acaagaggga gattcccgag   1140
gtgctcaaaa actctagatc tagacccgtg ggaacctcca tgttctgttt cgacggccct   1200
ctgacactcg tctcctataa gcccaagccc gccaagatgg tgtatctgct cagcagctgc   1260
gacgaagacg ccagcatcaa tgaatccacc ggcaagcccc agatggtcat gtactacaac   1320
cagaccaagg gaggcgtcga tacactggac cagatgtgtt ccgtcatgac atgctctaga   1380
aagaccaata gatggcccat ggctctgctg tacggcatga tcaacatcgc ttgcattaac   1440
tcctttatca tttactccca taacgtcagc tccaagggcg agaaggtgca gagcagaaag   1500
aaattcatga gaaatctgta catgagcctc accagcagct tcatgagaaa gaggctggag   1560
gcccccacac tgaaaagata tctgagagat aatatctcca acattctgcc taacgaggtc   1620
cccggcacaa gcgatgatag cacagaggag cccgtgatga agaagagaac atactgcaca   1680
tactgcccca gcaagattag aaggaaggcc aacgccagct gcaagaagtg caagaaggtc   1740
atctgcagag agcacaacat cgacatgtgc cagagctgtt tttga                   1785
```

<210> SEQ ID NO 7
<211> LENGTH: 1785
<212> TYPE: DNA
<213> ORGANISM: artificial
<220> FEATURE:
<223> OTHER INFORMATION: PB domain

<400> SEQUENCE: 7

```
atgggcagca gcctggacga cgagcacatc ctgagcgccc tgctgcagag cgacgacgag     60
ctggtcggcg aggacagcga cagcgaggtg agcgaccacg tgagcgagga cgacgtgcag    120
tccgacaccg aggaggcctt catcgacgag gtgcacgagg tgcagcctac cagcagcggc    180
tccgagatcc tggacgagca gaacgtgatc gagcagcccg gcagctccct ggccagcaac    240
aggatcctga ccctgcccca gaggaccatc aggggcaaga acaagcactg ctggtccacc    300
```

```
tccaagccca ccaggcggag cagggtgtcc gccctgaaca tcgtgagaag ccagaggggc    360

cccaccagga tgtgcaggaa catctacgac cccctgctgt gcttcaagct gttcttcacc    420

gacgagatca tcagcgagat cgtgaagtgg accaacgccg agatcagcct gaagaggcgg    480

gagagcatga cctccgccac cttcagggac accaacgagg acgagatcta cgccttcttc    540

ggcatcctgg tgatgaccgc cgtgaggaag gacaaccaca tgagcaccga cgacctgttc    600

gacagatccc tgagcatggt gtacgtgagc gtgatgagca gggacagatt cgacttcctg    660

atcagatgcc tgaggatgga cgacaagagc atcaggccca ccctgcggga gaacgacgtg    720

ttcacccccg tgagaaagat ctgggacctg ttcatccacc agtgcatcca gaactacacc    780

cctggcgccc acctgaccat cgacgagcag ctgctgggct tcaggggcag gtgcccottc    840

agggtctata tccccaacaa gcccagcaag tacggcatca agatcctgat gatgtgcgac    900

agcggcacca agtacatgat caacggcatg ccctacctgg gcaggggcac ccagaccaac    960

ggcgtgcccc tgggcgagta ctacgtgaag gagctgtcca agcccgtcca cggcagctgc   1020

agaaacatca cctgcgacaa ctggttcacc agcatccccc tggccaagaa cctgctgcag   1080

gagccctaca agctgaccat cgtgggcacc gtgagaagca acaagagaga gatccccgag   1140

gtcctgaaga acagcaggtc caggcccgtg ggcaccagca tgttctgctt cgacggcccc   1200

ctgaccctgg tgtcctacaa gcccaagccc gccaagatgg tgtacctgct gtccagctgc   1260

gacgaggacg ccagcatcaa cgagagcacc ggcaagcccc agatggtgat gtactacaac   1320

cagaccaagg gcggcgtgga caccctggac cagatgtgca gcgtgatgac ctgcagcaga   1380

aagaccaaca ggtggcccat ggccctgctg tacggcatga tcaacatcgc ctgcatcaac   1440

agcttcatca tctacagcca caacgtgagc agcaagggcg agaaggtgca gagccggaaa   1500

aagttcatgc ggaacctgta catgggcctg acctccagct tcatgaggaa gaggctggag   1560

gcccccaccc tgaagagata cctgagggac aacatcagca acatcctgcc caaagaggtg   1620

cccggcacca gcgacgacag caccgaggag cccgtgatga agaagaggac ctactgcacc   1680

tactgtccca gcaagatcag aagaaaggcc agcgccagct gcaagaagtg taagaaggtc   1740

atctgccggg agcacaacat cgacatgtgc cagagctgtt tctga                   1785
```

<210> SEQ ID NO 8
<211> LENGTH: 18
<212> TYPE: DNA
<213> ORGANISM: SV40

<400> SEQUENCE: 8

```
aagaagaaga gaaaggtg                                                   18
```

<210> SEQ ID NO 9
<211> LENGTH: 30
<212> TYPE: DNA
<213> ORGANISM: HIV

<400> SEQUENCE: 9

```
ggcagaaaga agagaagaca gagaagaaga                                      30
```

<210> SEQ ID NO 10
<211> LENGTH: 84
<212> TYPE: DNA
<213> ORGANISM: artificial
<220> FEATURE:
<223> OTHER INFORMATION: NSL domain -continued

<400> SEQUENCE: 10
ggcagaaaga agagaagaca gagaagaaga ccccccgccg gcaccagcgt gagcctgaag 60
aagaagagaa aggtgccccc cgcc 84

<210> SEQ ID NO 11
<211> LENGTH: 20
<212> TYPE: PRT
<213> ORGANISM: artificial
<220> FEATURE:
<223> OTHER INFORMATION: nucleic acid condensing peptide

<400> SEQUENCE: 11

Arg Gln Arg Gln Arg Tyr Tyr Arg Gln Arg Gln Arg Gly Gly Arg Arg
1               5                   10                  15

Arg Arg Arg Arg
            20

<210> SEQ ID NO 12
<211> LENGTH: 13
<212> TYPE: PRT
<213> ORGANISM: artificial
<220> FEATURE:
<223> OTHER INFORMATION: nucleic acid condensing peptide

<400> SEQUENCE: 12

Arg Gln Arg Gln Arg Gly Gly Arg Arg Arg Arg Arg Arg
1               5                   10

<210> SEQ ID NO 13
<211> LENGTH: 21
<212> TYPE: PRT
<213> ORGANISM: artificial
<220> FEATURE:
<223> OTHER INFORMATION: nucleic acid condensing peptide

<400> SEQUENCE: 13

Arg Arg Arg Arg Arg Arg Tyr Tyr Arg Gln Arg Gln Arg Gly Gly Arg
1               5                   10                  15

Arg Arg Arg Arg Arg
            20

<210> SEQ ID NO 14
<211> LENGTH: 39
<212> TYPE: PRT
<213> ORGANISM: artificial
<220> FEATURE:
<223> OTHER INFORMATION: nucleic acid condensing peptide

<400> SEQUENCE: 14

Gly Asn Gln Ser Ser Asn Phe Gly Pro Met Lys Gly Gly Asn Phe Gly
1               5                   10                  15

Gly Arg Ser Ser Gly Pro Tyr Gly Gly Gly Gly Gln Tyr Phe Ala Lys
            20                  25                  30

Pro Arg Asn Gln Gly Gly Tyr
        35

<210> SEQ ID NO 15
<211> LENGTH: 132
<212> TYPE: PRT
<213> ORGANISM: SV40

<400> SEQUENCE: 15

Asp Lys Val Leu Asn Arg Glu Glu Ser Leu Gln Leu Met Asp Leu Leu

-continued

```
1               5                   10                  15

Gly Leu Glu Arg Ser Ala Trp Gly Asn Ile Pro Leu Met Arg Lys Ala
            20                  25                  30

Tyr Leu Lys Lys Cys Lys Glu Phe His Pro Asp Lys Gly Gly Asp Glu
        35                  40                  45

Glu Lys Met Lys Lys Met Asn Thr Leu Tyr Lys Lys Met Glu Asp Gly
    50                  55                  60

Val Lys Tyr Ala His Gln Pro Asp Phe Gly Gly Phe Trp Asp Ala Thr
65                  70                  75                  80

Glu Ile Pro Thr Tyr Gly Thr Asp Glu Trp Glu Gln Trp Trp Asn Ala
                85                  90                  95

Phe Asn Glu Glu Asn Leu Phe Cys Ser Glu Glu Met Pro Ser Ser Asp
            100                 105                 110

Asp Glu Ala Thr Ala Asp Ser Gln His Ser Thr Pro Pro Lys Lys Lys
        115                 120                 125

Arg Lys Val Glu
    130
```

<210> SEQ ID NO 16
<211> LENGTH: 399
<212> TYPE: DNA
<213> ORGANISM: artificial
<220> FEATURE:
<223> OTHER INFORMATION: Cell division promoting domain

<400> SEQUENCE: 16

```
atggataaag ttttaaacag agaggaatct ttgcagctaa tggaccttct aggtcttgaa     60

aggagtgcct gggggaatat tcctctgatg agaaaggcat atttaaaaaa atgcaaggag    120

tttcatcctg ataaaggagg agatgaagaa aaaatgaaga aaatgaatac tctgtacaag    180

aaaatggaag atggagtaaa atatgctcat caacctgact ttggaggctt ctgggatgca    240

actgagattc caacctatgg aactgatgaa tgggagcagt ggtggaatgc ctttaatgag    300

gaaaacctgt tttgctcaga agaaatgcca tctagtgatg atgaggctac tgctgactct    360

caacattcta ctcctccaaa aaagaagaga aaggtagaa                           399
```

<210> SEQ ID NO 17
<211> LENGTH: 1824
<212> TYPE: DNA
<213> ORGANISM: artificial
<220> FEATURE:
<223> OTHER INFORMATION: modified piggyBac transposase

<400> SEQUENCE: 17

```
atgggcggca gaaagaagag aagacagaga agaagacccc ccgcctcctc cctcgatgac     60

gagcacattc tgtccgctct gctgcagtcc gacgatgagc tggtcggaga agacagcgat    120

agcgagatca gcgaccacgt ctccgaggac gacgtccaaa gcgacacaga ggaggccttc    180

atcgacgagg tgcacgaggt gcagcctacc agcagcggct ccgagatcct ggacgagcag    240

aacgtgatcg agcagcccgg cagctccctg gccagcaaca ggatcctgac cctgccccag    300

aggaccatca ggggcaagaa caagcactgc tggtccacct ccaagcccac caggcggagc    360

agggtgtccg ccctgaacat cgtgagaagc cagaggggcc ccaccaggat gtgcaggaac    420

atctacgacc ccctgctgtg cttcaagctg ttcttcaccg acgagatcat cagcgagatc    480

gtgaagtgga ccaacgccga gatcagcctg aagaggcggg agagcatgac ctccgccacc    540

ttcagggaca ccaacgagga cgagatctac gccttcttcg gcatcctggt gatgaccgcc    600
```

-continued gtgaggaagg acaaccacat gagcaccgac gacctgttcg acagatccct gagcatggtg 660
tacgtgagcg tgatgagcag ggacagattc gacttcctga tcagatgcct gaggatggac 720
gacaagagca tcaggcccac cctgcgggag aacgacgtgt tcacccccgt gagaaagatc 780
tgggacctgt tcatccacca gtgcatccag aactacaccc ctggcgccca cctgaccatc 840
gacgagcagc tgctgggctt caggggcagg tgccccttca gggtctatat ccccaacaag 900
cccagcaagt acggcatcaa gatcctgatg atgtgcgaca gcggcaccaa gtacatgatc 960
aacggcatgc cctacctggg caggggcacc cagaccaacg gcgtgcccct gggcgagtac 1020
tacgtgaagg agctgtccaa gcccgtccac ggcagctgca gaaacatcac ctgcgacaac 1080
tggttcacca gcatccccct ggccaagaac ctgctgcagg agccctacaa gctgaccatc 1140
gtgggcaccg tgagaagcaa caagagagag atccccgagg tcctgaagaa cagcaggtcc 1200
aggcccgtgg gcaccagcat gttctgcttc gacggccccc tgaccctggt gtcctacaag 1260
cccaagcccg ccaagatggt gtacctgctg tccagctgcg acgaggacgc cagcatcaac 1320
gagagcaccg gcaagcccca gatggtgatg tactacaacc agaccaaggg cggcgtggac 1380
accctggacc agatgtgcag cgtgatgacc tgcagcagaa agaccaacag gtggcccatg 1440
gccctgctgt acggcatgat caacatcgcc tgcatcaaca gcttcatcat ctacagccac 1500
aacgtgagca gcaagggcga gaaggtgcag agccggaaaa agttcatgcg gaacctgtac 1560
atgggcctga cctccagctt catgaggaag aggctggagg cccccaccct gaagagatac 1620
ctgagggaca acatcagcaa catcctgccc aaagaggtgc ccggcaccag cgacgacagc 1680
accgaggagc ccgtgatgaa gaagaggacc tactgcacct actgtcccag caagatcaga 1740
agaaaggcca gcgccagctg caagaagtgt aagaaggtca tctgccggga gcacaacatc 1800
gacatgtgcc agagctgttt ctga 1824

<210> SEQ ID NO 18
<211> LENGTH: 1869
<212> TYPE: DNA
<213> ORGANISM: artificial
<220> FEATURE:
<223> OTHER INFORMATION: modified piggyBac transposase

<400> SEQUENCE: 18
atgggcggca gaaagaagag aagacagaga agaagacccc ccgccggcac cagcgtgagc 60
ctgaagaaga agagaaaggt gccccccgcc tcctccctcg atgacgagca cattctgtcc 120
gctctgctgc agtccgacga tgagctggtc ggagaagaca gcgatagcga ggtgagcgac 180
cacgtctccg aggacgacgt ccaaagcgac acagaggagg ccttcatcga cgaggtgcac 240
gaggtgcagc ctaccagcag cggctccgag atcctggacg agcagaacgt gatcgagcag 300
cccggcagct ccctggccag caacaggatc ctgaccctgc cccagaggac catcaggggc 360
aagaacaagc actgctggtc cacctccaag cccaccaggc ggagcagggt gtccgccctg 420
aacatcgtga gaagccagag gggccccacc aggatgtgca ggaacatcta cgaccccctg 480
ctgtgcttca agctgttctt caccgacgag atcatcagcg agatcgtgaa gtggaccaac 540
gccgagatca gcctgaagag gcgggagagc atgacctccg ccaccttcag ggacaccaac 600
gaggacgaga tctacgcctt cttcggcatc ctggtgatga ccgccgtgag gaaggacaac 660
cacatgagca ccgacgacct gttcgacaga tccctgagca tggtgtacgt gagcgtgatg 720
agcagggaca gattcgactt cctgatcaga tgcctgagga tggacgacaa gagcatcagg 780

-continued cccaccctgc gggagaacga cgtgttcacc cccgtgagaa agatctggga cctgttcatc 840
caccagtgca tccagaacta cacccctggc gcccacctga ccatcgacga gcagctgctg 900
ggcttcaggg gcaggtgccc cttcagggtc tatatcccca acaagcccag caagtacggc 960
atcaagatcc tgatgatgtg cgacagcggc accaagtaca tgatcaacgg catgccctac 1020
ctgggcaggg gcacccagac caacggcgtg cccctgggcg agtactacgt gaaggagctg 1080
tccaagcccg tccacggcag ctgcagaaac atcacctgcg acaactggtt caccagcatc 1140
cccctggcca agaacctgct gcaggagccc tacaagctga ccatcgtggg caccgtgaga 1200
agcaacaaga gagagatccc cgaggtcctg aagaacagca ggtccaggcc cgtgggcacc 1260
agcatgttct gcttcgacgg ccccctgacc ctggtgtcct acaagcccaa gcccgccaag 1320
atggtgtacc tgctgtccag ctgcgacgag gacgccagca tcaacgagag caccggcaag 1380
ccccagatgg tgatgtacta caaccagacc aagggcggcg tggacaccct ggaccagatg 1440
tgcagcgtga tgacctgcag cagaaagacc aacaggtggc ccatggccct gctgtacggc 1500
atgatcaaca tcgcctgcat caacagcttc atcatctaca gccacaacgt gagcagcaag 1560
ggcgagaagg tgcagagccg gaaaaagttc atgcggaacc tgtacatggg cctgacctcc 1620
agcttcatga ggaagaggct ggaggccccc accctgaaga gatacctgag ggacaacatc 1680
agcaacatcc tgcccaaaga ggtgcccggc accagcgacg acagcaccga ggagcccgtg 1740
atgaagaaga ggacctactg cacctactgt cccagcaaga tcagaagaaa ggccagcgcc 1800
agctgcaaga agtgtaagaa ggtcatctgc cgggagcaca acatcgacat gtgccagagc 1860
tgtttctga 1869

<210> SEQ ID NO 19
<211> LENGTH: 486
<212> TYPE: DNA
<213> ORGANISM: artificial
<220> FEATURE:
<223> OTHER INFORMATION: modified piggyBac transposase

<400> SEQUENCE: 19
atgggcggca gaaagaagag aagacagaga agaagacccc ccgccggcac cagcgtgagc 60
ctgaagaaga agagaaaggt gccccccgcc gataaagttt taaacagaga ggaatctttg 120
cagctaatgg accttctagg tcttgaaagg agtgcctggg ggaatattcc tctgatgaga 180
aaggcatatt taaaaaaatg caaggagttt catcctgata aaggaggaga tgaagaaaaa 240
atgaagaaaa tgaatactct gtacaagaaa atggaagatg gagtaaaata tgctcatcaa 300
cctgactttg gaggcttctg ggatgcaact gagattccaa cctatggaac tgatgaatgg 360
gagcagtggt ggaatgcctt taatgaggaa aacctgtttt gctcagaaga aatgccatct 420
agtgatgatg aggctactgc tgactctcaa cattctactc ctccaaaaaa gaagagaaag 480
gtagaa 486

<210> SEQ ID NO 20
<211> LENGTH: 2298
<212> TYPE: DNA
<213> ORGANISM: artificial
<220> FEATURE:
<223> OTHER INFORMATION: modified piggyBac transposase

<400> SEQUENCE: 20
atgggcggca gaaagaagag aagacagaga agaagacccc ccgccggcac cagcgtgagc 60
ctgaagaaga agagaaaggt gccccccgcc gataaagttt taaacagaga ggaatctttg 120

-continued

```
cagctaatgg accttctagg tcttgaaagg agtgcctggg ggaatattcc tctgatgaga    180
aaggcatatt taaaaaaatg caaggagttt catcctgata aaggaggaga tgaagaaaaa    240
atgaagaaaa tgaatactct gtacaagaaa atggaagatg gagtaaaata tgctcatcaa    300
cctgactttg gaggcttctg ggatgcaact gagattccaa cctatggaac tgatgaatgg    360
gagcagtggt ggaatgcctt taatgaggaa aacctgtttt gctcagaaga aatgccatct    420
agtgatgatg aggctactgc tgactctcaa cattctactc ctccaaaaaa gaagagaaag    480
gtagaaggtg gtggtggttc tggtggtggt ggttcttcct ccctcgatga cgagcacatt    540
ctgtccgctc tgctgcagtc cgacgatgag ctggtcggag aagacagcga tagcgaggtg    600
agcgaccacg tctccgagga cgacgtccaa agcgacacag aggaggcctt tatcatcgac    660
gaggtgcacg aggtgcagcc taccagcagc ggctccgaga tcctggacga gcagaacgtg    720
atcgagcagc ccggcagctc cctggccagc aacaggatcc tgaccctgcc ccagaggacc    780
atcaggggca agaacaagca ctgctggtcc acctccaagc ccaccaggcg gagcagggtg    840
tccgccctga acatcgtgag aagccagagg ggccccacca ggatgtgcag gaacatctac    900
gaccccctgc tgtgcttcaa gctgttcttc accgacgaga tcatcagcga gatcgtgaag    960
tggaccaacg ccgagatcag cctgaagagg cgggagagca tgacctccgc caccttcagg   1020
gacaccaacg aggacgagat ctacgccttc ttcggcatcc tggtgatgac cgccgtgagg   1080
aaggacaacc acatgagcac cgacgacctg ttcgacagat ccctgagcat ggtgtacgtg   1140
agcgtgatga gcagggacag attcgacttc ctgatcagat gcctgaggat ggacgacaag   1200
agcatcaggc ccaccctgcg ggagaacgac gtgttcaccc ccgtgagaaa gatctgggac   1260
ctgttcatcc accagtgcat ccagaactac acccctggcg cccacctgac catcgacgag   1320
cagctgctgg gcttcagggg caggtgcccc ttcagggtct atatccccaa caagcccagc   1380
aagtacggca tcaagatcct gatgatgtgc gacagcggca ccaagtacat gatcaacggc   1440
atgccctacc tgggcagggg cacccagacc aacggcgtgc ccctgggcga gtactacgtg   1500
aaggagctgt ccaagcccgt ccacggcagc tgcagaaaca tcacctgcga caactggttc   1560
accagcatcc ccctggccaa gaacctgctg caggagccct acaagctgac catcgtgggc   1620
accgtgagaa gcaacaagag agagatcccc gaggtcctga agaacagcag gtccaggccc   1680
gtgggcacca gcatgttctg cttcgacggc cccctgaccc tggtgtccta caagcccaag   1740
cccgccaaga tggtgtacct gctgtccagc tgcgacgagg acgccagcat caacgagagc   1800
accggcaagc cccagatggt gatgtactac aaccagacca agggcggcgt ggacaccctg   1860
gaccagatgt gcagcgtgat gacctgcagc agaaagacca acaggtggcc catggccctg   1920
ctgtacggca tgatcaacat cgcctgcatc aacagcttca tcatctacag ccacaacgtg   1980
agcagcaagg gcgagaaggt gcagagccgg aaaaagttca tgcggaacct gtacatgggc   2040
ctgacctcca gcttcatgag gaagaggctg gaggccccca ccctgaagag atacctgagg   2100
gacaacatca gcaacatcct gcccaaagag gtgcccggca ccagcgacga cagcaccgag   2160
gagcccgtga tgaagaagag gacctactgc acctactgtc ccagcaagat cagaagaaag   2220
gccagcgcca gctgcaagaa gtgtaagaag gtcatctgcc gggagcacaa catcgacatg   2280
tgccagagct gtttctga                                                 2298
```

<210> SEQ ID NO 21
<211> LENGTH: 489
<212> TYPE: DNA

-continued

```
<213> ORGANISM: artificial
<220> FEATURE:
<223> OTHER INFORMATION: cell division promoting domain + NLS domain

<400> SEQUENCE: 21

atgggcggca gaaagaagag aagacagaga agaagacccc ccgccggcac cagcgtgagc      60

ctgaagaaga agagaaaggt gccccccgcc gataaagttt taaacagaga ggaatctttg     120

cagctaatgg accttctagg tcttgaaagg agtgcctggg ggaatattcc tctgatgaga     180

aaggcatatt taaaaaaatg caaggagttt catcctgata aaggaggaga tgaagaaaaa     240

atgaagaaaa tgaatactct gtacaagaaa atggaagatg gagtaaaata tgctcatcaa     300

cctgactttg gaggcttctg ggatgcaact gagattccaa cctatggaac tgatgaatgg     360

gagcagtggt ggaatgcctt taatgaggaa aacctgtttt gctcagaaga aatgccatct     420

agtgatgatg aggctactgc tgactctcaa cattctactc ctccaaaaaa gaagagaaag     480

gtagaatga                                                             489


<210> SEQ ID NO 22
<211> LENGTH: 5
<212> TYPE: PRT
<213> ORGANISM: artificial
<220> FEATURE:
<223> OTHER INFORMATION: synthetic peptide

<400> SEQUENCE: 22

Arg Gln Arg Gln Arg
1               5


<210> SEQ ID NO 23
<211> LENGTH: 6
<212> TYPE: PRT
<213> ORGANISM: artificial
<220> FEATURE:
<223> OTHER INFORMATION: synthetic peptide

<400> SEQUENCE: 23

Arg Arg Arg Arg Arg Arg
1               5
```